(12) United States Patent  
Yedlicka et al.

(10) Patent No.: US 8,480,673 B2
(45) Date of Patent: Jul. 9, 2013

(54) CAVITY CREATION DEVICE AND METHODS OF USE

(75) Inventors: Joseph W. Yedlicka, Indianapolis, IN (US); Robert A. Till, Jr., Avon, IN (US); Nancy S. Yedlicka, Indianapolis, IN (US); Patricia M. Till, Avon, IN (US)

(73) Assignee: Osteo Innovations LLC, Indianapolis, IN (US)

( * ) Notice: Subject to any disclaimer, the term of this patent is extended or adjusted under 35 U.S.C. 154(b) by 1606 days.

(21) Appl. No.: 11/788,415

(22) Filed: Apr. 20, 2007

(65) Prior Publication Data

US 2007/0282345 A1    Dec. 6, 2007

Related U.S. Application Data

(60) Provisional application No. 60/809,945, filed on Jun. 1, 2006.

(51) Int. Cl.
 *A61B 17/70* (2006.01)
(52) U.S. Cl.
 USPC ............................................. 606/80
(58) Field of Classification Search
 USPC .............. 606/79–81; 433/118, 119, 165, 166, 433/124, 133; 408/36, 141
 See application file for complete search history.

(56) References Cited

U.S. PATENT DOCUMENTS

| | | | | |
|---|---|---|---|---|
| 2,243,718 A * | 5/1941 | Moreira | | 606/80 |
| 5,030,222 A * | 7/1991 | Calandruccio et al. | | 606/96 |
| 5,041,119 A * | 8/1991 | Frigg et al. | | 606/96 |
| 5,269,785 A * | 12/1993 | Bonutti | | 606/80 |
| 5,779,708 A * | 7/1998 | Wu | | 606/80 |
| 5,913,867 A * | 6/1999 | Dion | | 606/180 |
| 6,679,886 B2 * | 1/2004 | Weikel et al. | | 606/79 |
| 6,746,451 B2 * | 6/2004 | Middleton et al. | | 606/79 |
| 7,641,658 B2 * | 1/2010 | Shaolian et al. | | 606/80 |
| 2001/0031967 A1 * | 10/2001 | Nicholson et al. | | 606/84 |
| 2002/0133148 A1 | 9/2002 | Daniel et al. | | |
| 2002/0188299 A1 * | 12/2002 | Reiley et al. | | 606/79 |
| 2003/0233096 A1 * | 12/2003 | Osorio et al. | | 606/86 |
| 2005/0113836 A1 * | 5/2005 | Lozier et al. | | 606/80 |
| 2010/0057087 A1 * | 3/2010 | Cha | | 606/80 |

* cited by examiner

*Primary Examiner* — Mary Hoffman
(74) *Attorney, Agent, or Firm* — Mark S. Leonardo; Brown Rudnick LLP

(57) ABSTRACT

A cavity drill is provided, which is configured for use with a bone drill. The cavity drill includes a body. The bone drill has a first portion movably connected to a second portion. A third portion is movably connected to the second portion. The body is mounted with the third portion of the bone drill. A sheath extends from the third portion to a distal end. A curette is connected with the distal end of the bone drill. The curette is composed of retractable cutting tines/blades which are turned/powered by the bone drill motor. The curette tines can be used in a partially or fully deployed state and at low or high speed. The curette is designed to create cavities of varying size in a bone. The cavity drill and the bone drill may include a radiation protection guard and radiolucent portions. Methods of use are also provided.

21 Claims, 29 Drawing Sheets

CAVITY CREATION DEVICE AND METHODS OF USE

CROSS REFERENCE TO RELATED APPLICATIONS

This patent application claims the benefit of U.S. Provisional Patent Application Ser. No. 60/809,945, filed on Jun. 1, 2006, the contents of which being incorporated herein by reference in its entirety.

I. BACKGROUND OF THE INVENTION

A. Field of the Invention

The present disclosure relates to medical devices, components, and methods for use thereof, such as bone drills, bone drill assemblies, bone impact drills, bone cavity creation/enlargement devices, guide forceps, and fluid transfer devices especially those for treating vertebral body and sacral fractures, as well as lytic (destructive) tumor deposits in bone, for use in bone biopsies/bone infusions, for procedures requiring bone access and for use in medical procedures requiring a drill driven screwdriver or similar tools especially when there is a need for an off-angle, largely translucent bone access device having radiation protection for the operator designed to be used with X-ray (fluoroscopic) guidance and when there is a need for an improved device for creating/enlarging a cavity in a bone.

B. Background Information

Throughout the years and most recently in particular, various instruments have been developed for use in and for particular medical procedures and/or techniques requiring bone access. In some bone access procedures, it is necessary to create one or more holes in a bone or bone sections or to bore through the bone. Medical instruments known as bone drills have been developed for creating such holes and bores. Other instruments such as catheters, needles, guide needles, curettes and the like may then be introduced into the hole. On occasion, a cavity needs to be created or enlarged within the bone to facilitate treatment of a bone lesion.

Examples of medical procedures or techniques performed with fluoroscopic (X-ray) guidance that require drilling into bone (and thus the use of a bone drill) and often require creating a cavity or enlarging a cavity in the bone include vertebroplasty and/or vertebral augmentation procedures, sacroplasty, osteoplasty, and bone biopsies/infusions. Other medical procedures require the use of drill-driven screwdrivers or similar tools which may need to be used with X-ray (fluoroscopic) guidance.

Vertebroplasty is a procedure for treating vertebral body (spinal) compression fractures. Sacroplasty is a procedure for treating sacral fractures. Osteoplasty is a procedure for treating painful lytic (destructive) tumor deposits in bone. Osteoporosis is the most common cause for vertebral compression fractures and sacral fractures, however, bone tumors involving the spine such as multiple myeloma and metastatic disease can also cause these fractures. A vertebral body compression fracture (VCF) is a fracture involving the vertebral body which causes the vertebral body to be compressed or to collapse. This can lead to shortening and tilting of the spinal column with a forward curvature. This forward curvature can lead to pulmonary and gastrointestinal complications. These fractures are extremely painful and debilitating with many of these patients needing wheelchairs for less painful ambulation; many of these patients are bed-ridden. Vertebroplasty is designed to stabilize VCFs and relieve pain. Vertebral height restoration and deformity reduction are also desired.

In vertebral augmentation and vertebroplasty, access needles are manually pushed or hammered into the fractured vertebral body using fluoroscopic (X-ray) guidance. Various instruments such as a curette may then be inserted through the access needles or tubes. At that point in vertebroplasty, an orthopedic bone filler/cement (e.g. PMMA) is instilled into the fractured bone. However, in vertebral augmentation, before the bone cement is instilled, balloon catheters are inserted through the access needles or tubes into the fractured vertebral body and inflated in an attempt to restore the compressed/collapsed vertebral body to its original height and also to create a cavity in the fractured bone. Following the balloon dilation, the balloons are removed and thicker bone cement is instilled into the fractured vertebral body through the access needles or tubes. The cement hardens quickly for both procedures, providing strength and stability to the vertebra. The progress of both procedures is continually monitored in real time with fluoroscopic (X-ray) guidance.

In sacroplasty, access needles are manually pushed or hammered into the fractured sacrum using fluoroscopic (X-ray) or computed tomographic (CT) guidance. Cavity creation in the bone is often necessary. Various instruments such as curettes or balloons may then be inserted through the access needles in order to create/enlarge a cavity in the bone. An orthopedic bone filler/cement (e.g. PMMA) is then instilled through the access needles/tubes into the fractured sacrum. This has been found to provide pain relief and stability. Procedural progress is continually monitored with CT and/or fluoroscopic guidance.

In osteoplasty, access needles are manually pushed or hammered into the lytic (destructive) bone tumor deposit using fluoroscopic (X-ray) or computed tomographic (CT) guidance. Cavity creation in the bone may be necessary. Various instruments such as curettes, balloons, or radiofrequency (RF) probes may be inserted through the access needles. An orthopedic bone filler/cement (e.g.) PMMA is then instilled through the access needles/tubes into the lytic deposit. This has been found to provide pain relief and stability. Procedural progress is continually monitored with CT and/or fluoroscopic guidance.

In bone biopsies, needles are manually pushed or hammered into the bone in order to obtain a specimen. In bone infusions, needles are manually pushed or hammered into the bone in order to achieve bone access. Cavity creation in the bone may be of benefit in bone biopsies and infusions.

It has been recognized that it would be desirable for a bone drill/impact drill to place the access needles in the targeted bone in a single step using fluoroscopic (X-ray) or CT guidance. It has also been recognized that it is desirable for this bone drill/impact drill to have a guide tube or access needle in conjunction with a drill bit, the guide tube surrounding the drill bit. The guide tube/access needle may then be used as a conduit into the targeted bone. This drill/impact drill can also be used with various bits (such as a screwdriver) for various medical procedures. However, existing drills suffer from various design defects that make them unsuitable to be used with fluoroscopic (X-ray) or computed tomographic (CT) guidance for these procedures. It is often difficult to place needles or access devices into bone by manually pushing or hammering; also the currently used devices result in excessive radiation exposure to the operator (particularly the hands). Also, currently available bone curettes do not reliably create a cavity in the accessed bone and also result in excessive radiation exposure to the operator (particularly the hands). It is recognized that the above mentioned procedures (vertebral augmentation, vertebroplasty, sacroplasty, and osteoplasties) may result in leakage of bone filler/cement through cracks in the targeted bone into undesired areas adjacent to the targeted bone such as the intervertebral disc, spinal canal, neural foramina, and blood vessels. This disadvantageously can result in undesirable health risk to the patient. Thus, it is recognized that it is desirable for an improved cavity creation/enlargement drill/device which would reduce the risk of undesirable filler/cement/fluid leak from the targeted bone.

It is thus evident from the above that there is a need for an improved bone drill and related methods of use. It is evident that there is a need for improved drill bits to be used for these applications. It is evident from the above that there is a need for improved devices that create/enlarge cavities in the targeted bone. It is evident from the above that there is a need for a guide forceps to be used with these devices. It is evident from the above that there is need for a fluid transfer device to be used with these devices. It is also evident that there is a need for operator radiation protection when using these devices.

II. SUMMARY OF THE INVENTION

An off-angle, largely translucent bone access drill having a cavity drill is provided for placing in one step an access needle/tube/conduit into targeted bone. The drill also has radio opaque markers allowing more accurate alignment of the bone drill during use under fluoroscopic guidance. These attributes allow more accurate, rapid, and safe placement of the access needle/tube/conduit into the targeted bone. The present disclosure also reduces radiation exposure to the physician by allowing his/her hands to be further from the radiation source and patient. Radiation protection to the operator's hand is also provided by a radiation protection guard on the drill handle. Further, a cavity creation/enlargement device is disclosed to be inserted into and powered by the bone drill to allow more accurate, rapid, and safe cavity creation/enlargement in the affected bone. The drill is also designed to be used with various bits (e.g. screwdriver) for various medical procedures.

In one form, there is provided a bone drill which powers a snap-in, quick release cavity creation/enlargement device for performing the various medical procedures (e.g., vertebroplasty and/or vertebral augmentation procedures, sacroplasty, osteoplasty, bone biopsies/infusions, and other procedures requiring the use of such a drill/impact drill and cavity creation/enlargement device). Portions of the bone drill are radiolucent, while radio opaque markers allow alignment of the bone drill during use (e.g. under fluoroscopy). At least a head portion of the bone drill is formed of the radiolucent material while a drill bit and access needle/sheath/conduit are formed of a radio opaque material. The drill is off-angle reducing radiation exposure by allowing for the operator's hands to be kept out of and further away from the path of the primary X-rays. A radiation protection hand guard on the drill handle provides additional radiation protection to the operator's hand.

In one form, there is provided a bone drill having a cavity drill assembly especially for performing the above described bone procedures. The bone drill assembly includes a drilling assembly including a drill bit and sheath assembly extending over/outside the drill bit. The sheath assembly is rotated independent of the drill bit and subsequent to drilling of a hole to a partial depth by the drill bit. An oversized hole is created that retains the sheath assembly for use as an instrument tube/conduit.

Also provided is a cavity creation/enlargement device designed to be inserted into the bone drill and driven by the bone drill. In one particular embodiment, in accordance with the principles of the present disclosure, a cavity drill/creation/enlargement device is provided, which is configured for use with a bone drill. The cavity drill includes a body. The bone drill has a first portion movably connected to a second portion. A third portion is movably connected to the second portion. The body is mounted with the third portion of the bone drill. A cavity drill is affixed to the third portion of the bone drill. The cavity drill includes a tubular body/pusher/cutter within an outer tube and an end cap. The other end includes a plastic molded handle with snapping features to lock and release from the bone drill. Inside the outer tube is a pusher/cutting tube having its end cut to create a plurality of cutting blades. Holes allow the curette blades to be pushed out from the outer tube. A pusher controls the extension of the curette blades. Guides in the end cap aid in directing the blades. The tubular shaft assembly is inserted into the bone drill with the bone drill causing the blades to turn and create/enlarge a cavity in the targeted bone. The cutting blades may have radio opaque markers to increase conspicuity. The body supports gearing that operatively couples the sheath to a motor of the bone drill for rotation of the sheath. The sheath may be configured to rotate continuously in one direction or the other, or in an oscillating configuration such that the sheath rotates in a clockwise direction and in a counterclockwise direction.

At least a portion of the cavity creation/enlargement drill may be radiolucent. The cavity drill may include radio opaque markers configured for alignment of the sheath during a fluoroscopy procedure. The body can be formed of the radiolucent material and the sheath formed of a radio opaque material. The curette may be introduced into the targeted bone through the access conduit/sheath/tube placed into the bone with the bone drill.

The cavity drill may include a handle extending from the body. The handle is connected with the curette wherein the handle is manipulable in a configuration that causes movement of the curette's cutting blades. The handle can be connected to the curette in a gearing disposed with the body.

The sheath may be configured to rotate in an oscillating configuration such that the distal end rotates in a clockwise direction and a counterclockwise direction. The sheath can be configured for axial movement relative to the body. The third portion may be disposed at an angular orientation relative to the first portion of the bone drill. The cavity drill may include a radiation protection guard mounted to the bone drill.

In another embodiment, a bone drill configured for treating bone of a vertebral body is provided. The bone drill includes a handle connected to a drive housing. The drive housing is connected to a head portion. The head portion includes a shaft extending therefrom. The shaft includes a drill bit and a sheath disposed about the drill bit. The shaft is coupled to a motor disposed with the drive housing via gearing such that the motor rotates the drill bit and the sheath. A cavity drill is mounted with the head portion and includes the sheath. The sheath has a curette disposed at a distal end thereof.

The head portion may include radio opaque markers disposed in a configuration to facilitate alignment of the shaft during a fluoroscopy procedure.

In another embodiment, a cavity drill configured for use with a bone drill is provided. The cavity drill includes a body having a sheath extending therefrom and being mounted with the bone drill. The body supports gearing that operatively couples the sheath to a motor of the bone drill for rotation of the sheath. A cutting blade extends from the sheath and is configured to rotate in an oscillating configuration such that the cutting blade rotates in a clockwise direction and a counterclockwise direction.

The sheath can be configured for axial movement relative to the body. The axial movement may be spring driven to facilitate impact engagement of the sheath with bone of vertebral body. The cavity drill can include a handle extending from the body. The handle is connected with the curette wherein the handle is manipulable in a configuration that causes movement of a curette being disposed with a distal end of the sheath.

The gearing may be configured to convert a rotation of the motor to oscillation of the cutting blade. The cutting blade may excise a defined arc in bone. The defined arc is approximately 60 degrees.

The present disclosure provides an off-angle bone drill that reduces radiation exposure to the operator by allowing his/her hands and body to be further from the primary radiation source and the patient (scatter radiation). A radiation protection hand guard on the drill handle also provides radiation protection to the operator's hand(s). The bone drill is also largely radiolucent with radio opaque markers for aligning the bone drill. Moreover, the drill and sheath assembly provide bone drilling and conduit insertion in one step. The present disclosure also provides a cavity creation/enlargement tool or device (curette). The curette may be used in conjunction with the present bone drill assembly.

The various aspects of the present disclosure will be more apparent upon reading the following detailed description in conjunction with the accompanying drawings.

III. BRIEF DESCRIPTION OF THE DRAWINGS

The above-mentioned and other features and objects of this disclosure, and the manner of attaining them, will become more apparent and the disclosure itself will be better understood by reference to the following description of embodiments of the disclosure taken in conjunction with the accompanying drawings, wherein.

Like reference numerals indicate the similar parts throughout the figures.

IV. DETAILED DESCRIPTION OF EMBODIMENTS OF THE INVENTION

The exemplary embodiments of the bone drill and methods of use disclosed are discussed in terms of medical apparatus and more particularly, in terms of bone drills, bone drill assemblies and bone cavity drills that can be employed for treating vertebral body and sacral fractures. The bone drill may also be employed to treat lytic tumor deposits in bone. It is envisioned that the present disclosure may be employed with a range of applications including vertebroplasty and/or vertebral augmentation procedures, sacroplasty and osteoplasty. The bone curette is designed with snapping features to lock and release from the bone drill; the bone drill turns/powers the curette blades. The curette blades may have radio opaque markers to increase conspicuity. The curette can be used to create a cavity inside a bone for various medical applications and treatment procedures. It is envisioned that the present disclosure may be used to provide access for bone biopsies and bone infusions. It is also envisioned that these devices may be used with different drill bits (such as screwdrivers) for various medical procedures. It is further envisioned that the present disclosure may be used with other medical applications such as diagnosis, treatment and surgery.

Figure 1:
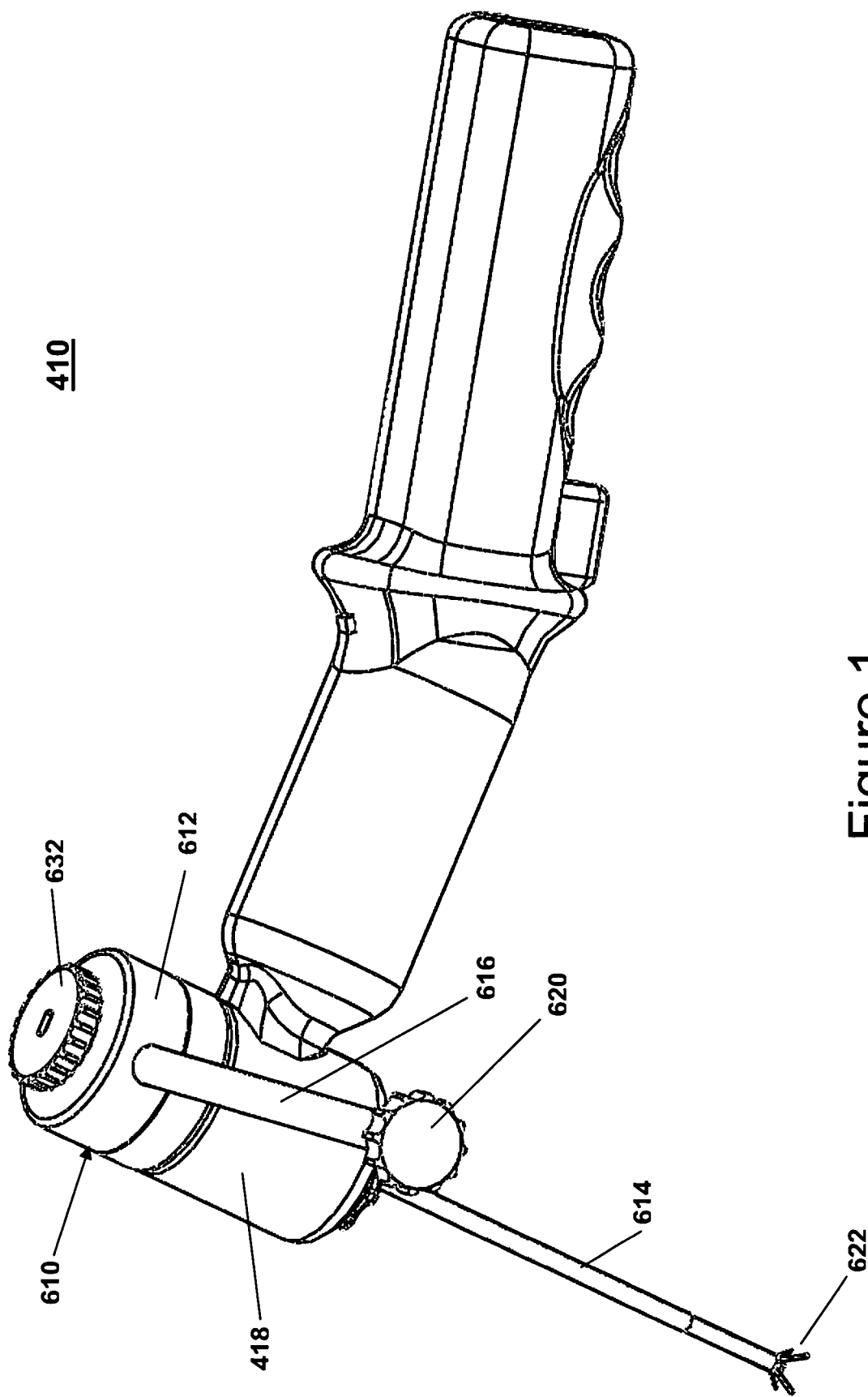
FIG. 1 is a perspective view of one particular embodiment of a bone drill having a cavity drill constructed in accordance with the principles of the present disclosure.
Figure 2:
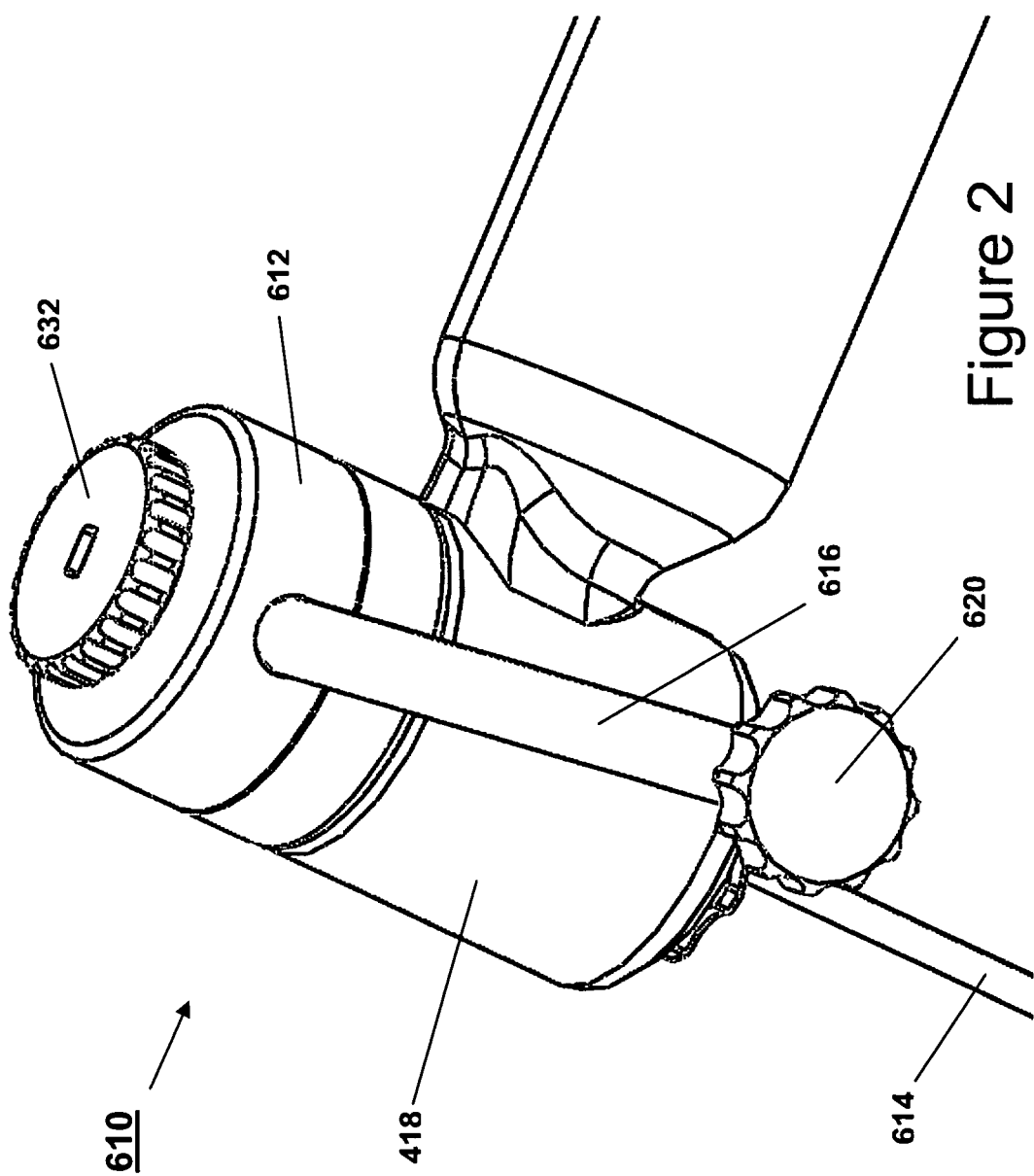
FIG. 2 is an enlarged top perspective cutaway view of a head portion of the bone drill shown in FIG. 1.

The following discussion includes a description of a bone drill having a cavity drill, related components and exemplary methods of operating the bone drill in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated a cavity drill 610 configured for use with a bone drill 410, in accordance with the principles of the present disclosure. See, for example, a description of bone drill 410 and other usable bone drills described in co pending and commonly owned U.S. Utility patent application Ser. No. 11/788,413, filed on Apr. 20, 2007 under Express Mail Label No. ER 550793142 US, the contents of which being incorporated herein by reference in its entirety.

The components of bone drill 410 are fabricated from materials suitable for medical applications, such as, for example, polymerics and/or metals, depending on the particular application and/or preference. Semi-rigid and rigid polymerics are contemplated for fabrication, as well as resilient materials, such as molded medical grade polyurethane, etc. The motors, gearing, electronics and power components of bone drill 410 may be fabricated from those suitable for a medical application. Bone drill 410 may also include circuit boards, circuitry, processor components, etc. for computerized control. One skilled in the art, however, will realize that other materials and fabrication methods suitable for assembly and manufacture, in accordance with the present disclosure, also would be appropriate.

Detailed embodiments of the present disclosure are disclosed herein, however, it is to be understood that the described embodiments are merely exemplary of the disclosure, which may be embodied in various forms. Therefore, specific functional details disclosed herein are not to be interpreted as limiting, but merely as a basis for the claims and as a representative basis for teaching one skilled in the art to variously employ the present disclosure in virtually any appropriately detailed embodiment.

Cavity drill 610 and bone drill 410 are adapted to bore a hole into bone such as, for example, into a vertebra or vertebral body during a vertebroplasty procedure and under fluoroscopy. As such, various components, as desired, of cavity drill 610 and bone drill 410, are formed of a radio translucent (radiolucent) material. Thus, only those components that are not radiolucent will show up under x-ray and/or during real time fluoroscopy. It should be appreciated that bone drill 410 including cavity drill 610 is adapted to perform various surgical drilling procedures other than for a vertebroplasty procedure.

In one form, bone drill 410 is adapted to create or drill a bore in bone of a vertebral or sacral body, and to introduce and temporarily leave a tube, tubular sheath or the like in the bore. A tubular sheath of the bone drill assembly is configured to allow an instrument, component, tool or the like to pass therethrough and provide access to an area at or adjacent to the distal end of the tubular sheath.

In operation, a bone drill having a cavity drill, similar to those described herein, is employed with a method for treating bone of a vertebral body or a sacral body. See, for example, the description of methods of use described in co pending and commonly owned U.S. Utility patent application Ser. No. 11/788,413, filed on Apr. 20, 2007 under Express Mail Label No. ER 550793142 US.

Referring to FIGS. 1-8, cavity drill 610 includes a body 612, a sheath 614 and a handle 616. It is also envisioned that cavity drill 610, or components thereof, are disposable after a vertebral body or sacral body procedure. Cavity drill 610 and its components may also be reused.

Cavity drill 610 is assembled by removing a drill bit handle and a sheath of bone drill 410, and attaching cavity drill 610 thereafter. The cavity drill may then be inserted through the access sheath/conduit/tube previously placed by the off-angle bone drill to reach the affected bone area. Body 612 mounts to head 418 via tabs 618, which are snapped or inserted with corresponding slots of head 418. Upon attachment, sheath 614 extends through a support cylinder of bone drill 410. Cavity drill 610 is mounted for rotation relative to head 418.

The cavity drill is powered by the drill motor of bone drill 410. The act of mounting cavity drill 610 to the head 418 connects the drive mechanism within head 418 to the sheath 614 through a spline type interface. Activating the drill motor causes the sheath 614 to rotate which in turn rotates the cutter 622. As the cutter is rotating, the blades 642 stored within the cutter 622 can be extended or retracted as desired to cut the desired cavity diameter.

Handle 616 extends laterally from body 612 to a knob 620. Handle 616 is configured to facilitate remote manipulation of knob 632 from a distance that allows the users hands to remain away from the radiation beam while adjusting the cutter extension. Knob 620 is knurled to facilitate manipulation thereof. Rotating knob 632 directly or remotely using knob 620, causes the cutter blades to extend or retract thereby defining the size of the cavity being cut for creating and/or enlarging a cavity in targeted bone.

Figure 6:
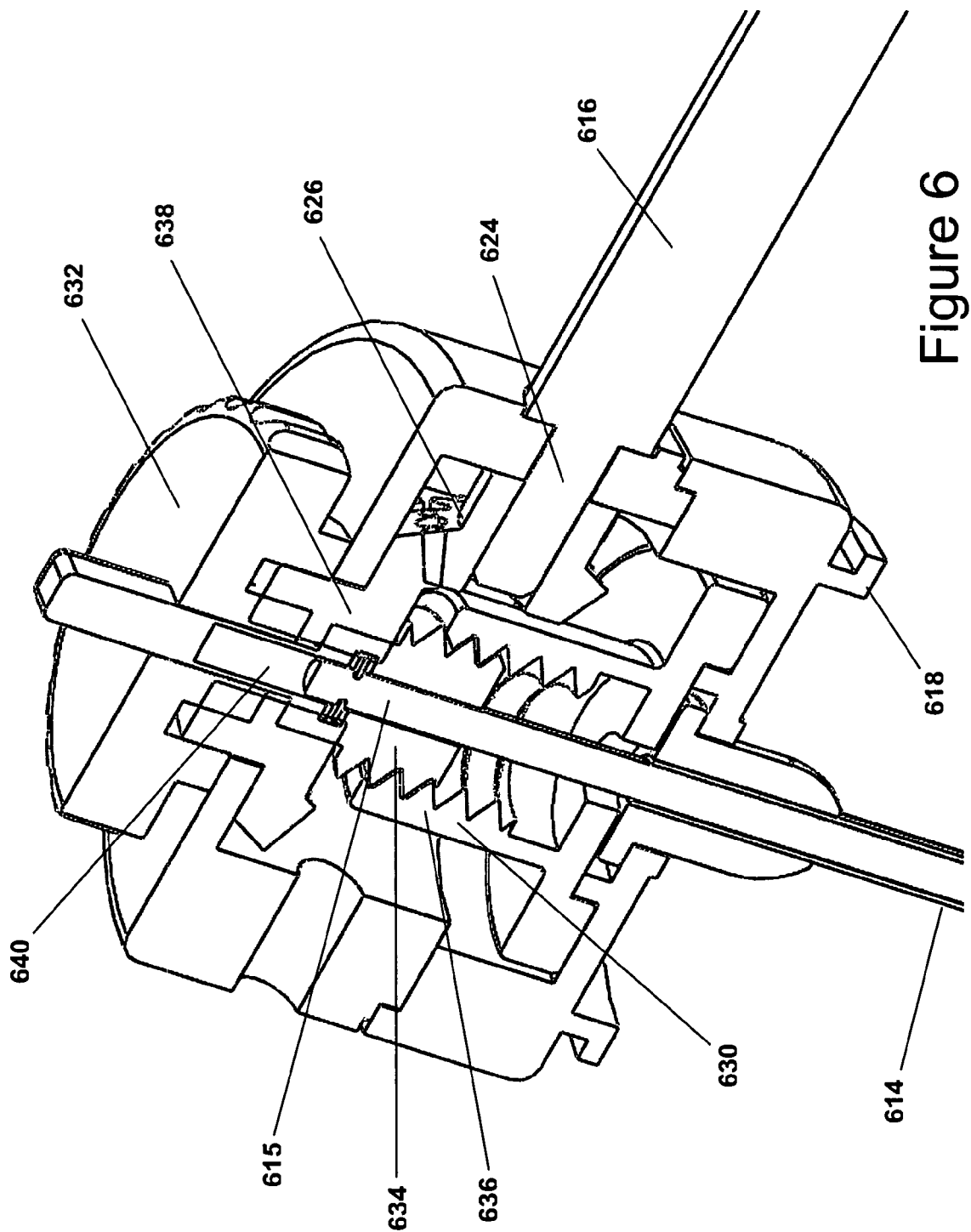
FIG. 6 is a side enlarged view, in cross section of a head portion of the cavity drill shown in FIG. 4.
Figure 7:
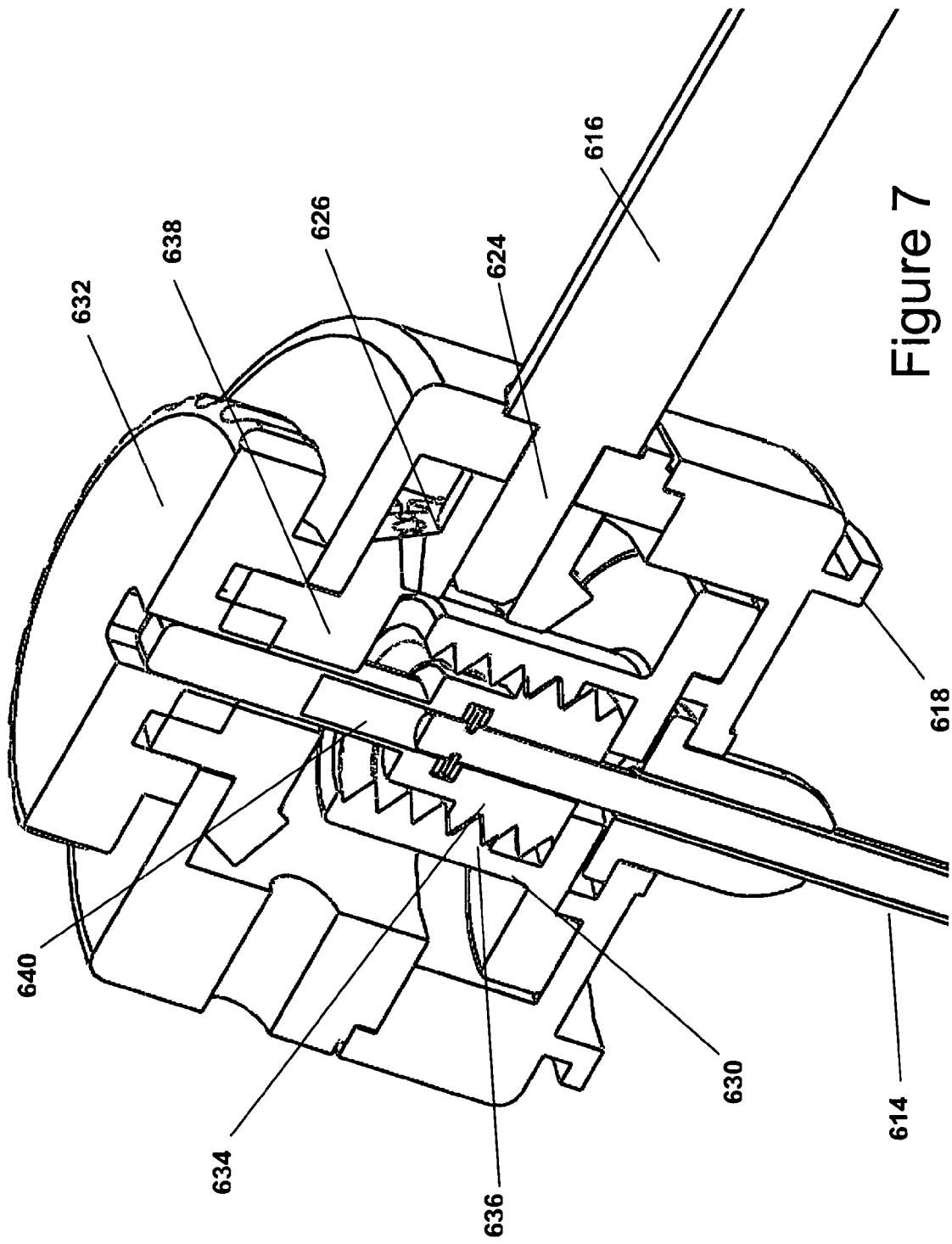
FIG. 7 is a side enlarged view, in cross section of the head portion shown in FIG. 4.
Figure 8:
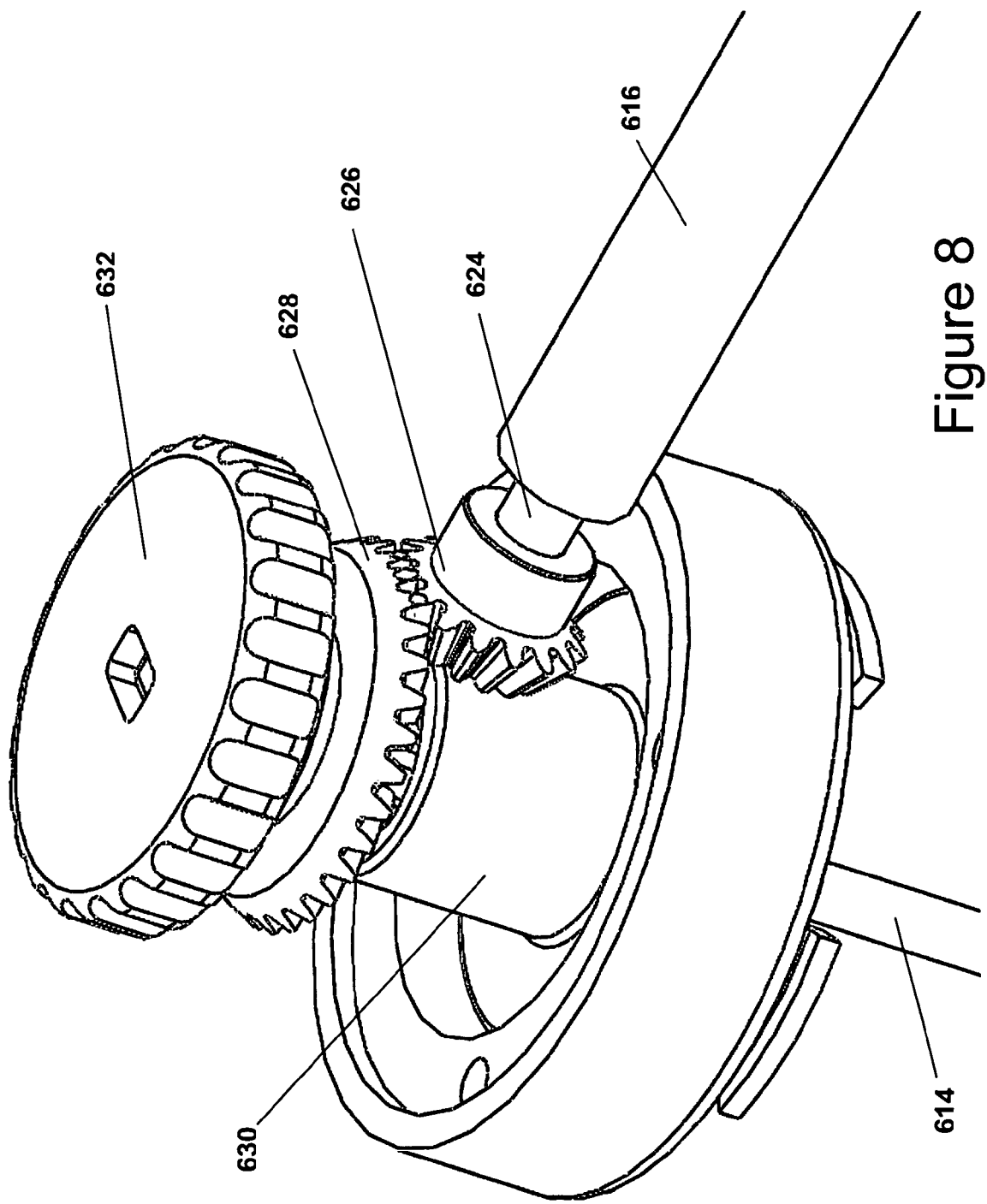
FIG. 8 is an enlarged view of the head portion shown in FIG. 4, with a body portion removed.

Referring to FIG. 6, handle 616 includes an output shaft 624, mounted with a bevel gear 626, which translates rotation of handle 616 to the gearing of body 612. Bevel gear 626 meshes with an input gear 638 of the gearing of body 612. Input gear 638 is mated to knob 632 through the upper housing of body 612. Input gear 638 includes teeth radially disposed thereabout that mesh with teeth of bevel gear 626. As bevel gear 626 rotates, as caused by rotation of handle 616 described above, input gear 638 is caused to rotate, which in turn rotates knob 632. Knob 632 is knurled to facilitate manipulation thereof. Knob 632 is disposed for extension and retraction of cutter blades 642 of bone curette 622. Knob 632 is slidably mounted to push rod 615 through a male gear 634, which mates with a female gear 636 of support cylinder 630. Male gear 634 and female gear 636 are correspondingly threaded for reciprocal rotation and relative axial movement. As knob 632 is manipulated for rotation, male gear 634 threadably engages with female gear 636. The reciprocal rotation of gears 634, 636 causes relative axial translation of male gear 634 and thus push rod 615 inside of sheath 614, which freely rotates within a cavity 640 of gear 634. This configuration advantageously facilitates driving of cutter blades 642 within bone curette 622 into the targeted bone for a procedure. For example, as shown in FIG. 6, push rod 615 is in a retracted position. Knob 632 is rotated to cause axial movement of push rod 615 to an extended position as described, as shown in FIG. 7.

Figure 3:
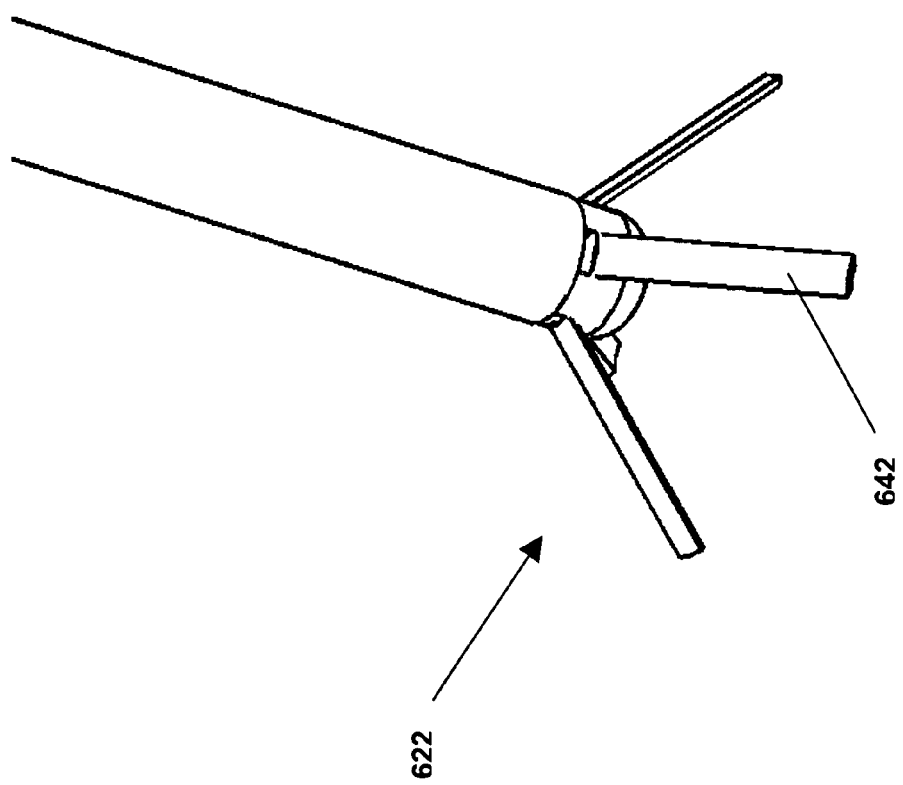
FIG. 3 is a perspective cutaway view of a distal portion of a bone curette constructed in accordance with the principles of the present disclosure.
Figure 4:
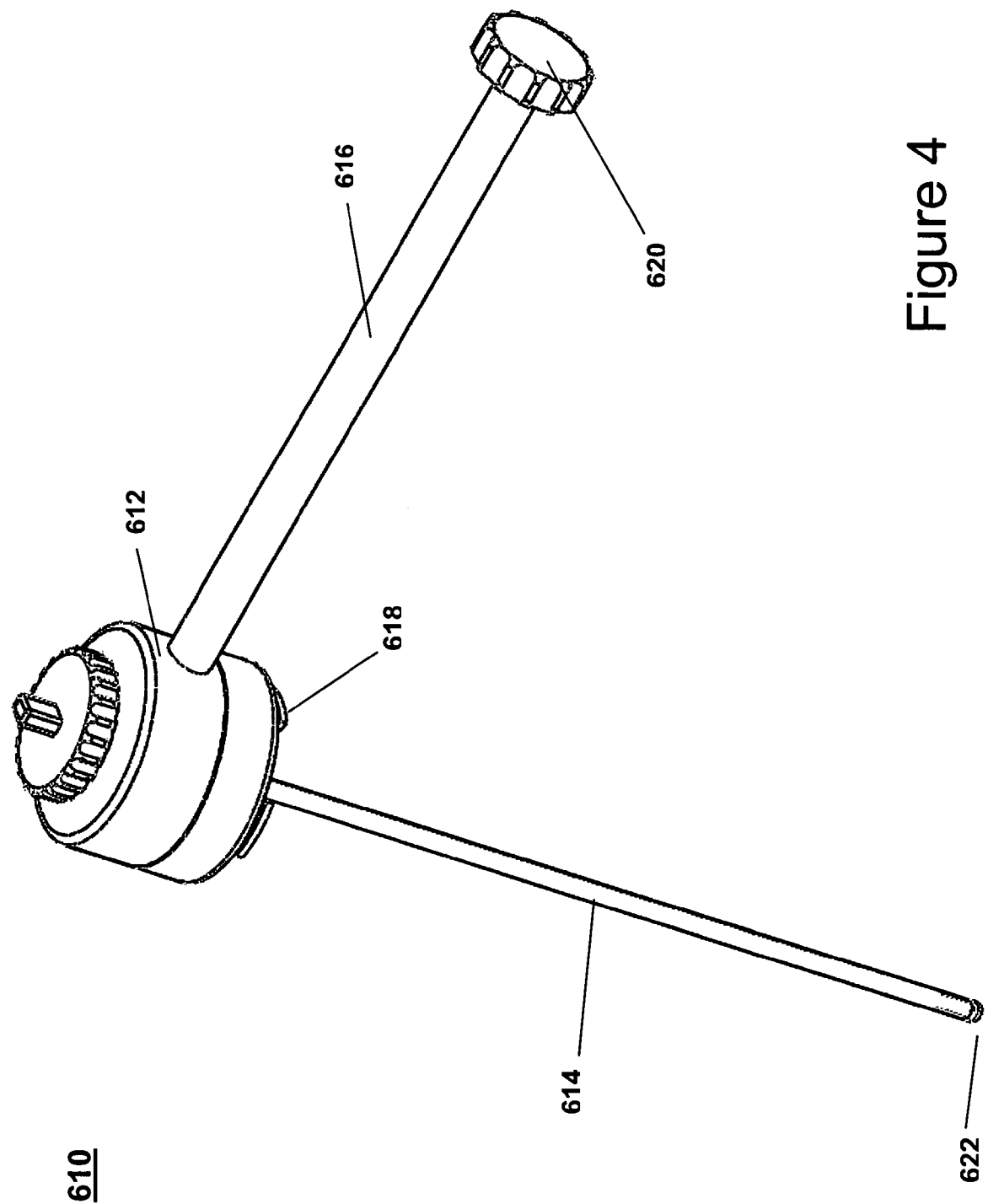
FIG. 4 is a perspective view of a cavity drill shown in FIG. 1, separated from the bone drill.
Figure 5:
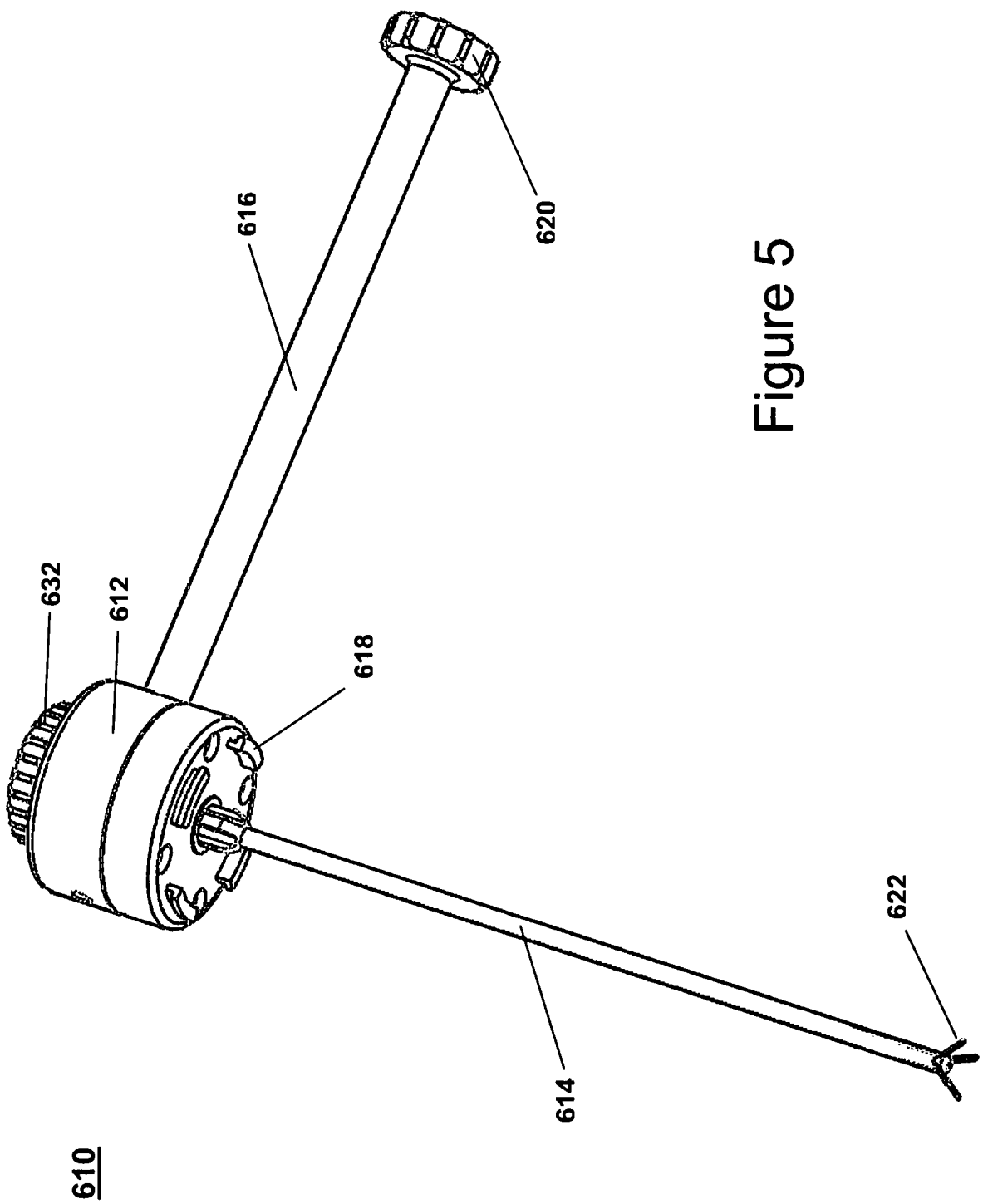
FIG. 5 is a side perspective view of the cavity drill shown in FIG. 4.

Bone curette 622 includes blades 642, as shown in FIG. 3. Blades 642 have a wide, thin design to facilitate cutting of the targeted bone. Blades 642 rotate to cut the targeted bone. Rotation is controlled and powered by motor 498. Blades 642 are advanced and retracted by manipulating knob 632, as described above. Blades 642 are flexible in one direction, allowing them to deflect out of the holding position at an angle as they extend. The length of extension and the deflection angle define the diameter of the cutting action. The blades are wider and thereby stiffer/stronger in the circumferential direction to facilitate cutting of the bone without deflection. The ends of the blades may have a plurality of different cutting edges defined as desired. Blades 642 may have radio-opaque markers to facilitate alignment of cavity drill 610 and visual determination of cavity size/length being created.

Figure 9:
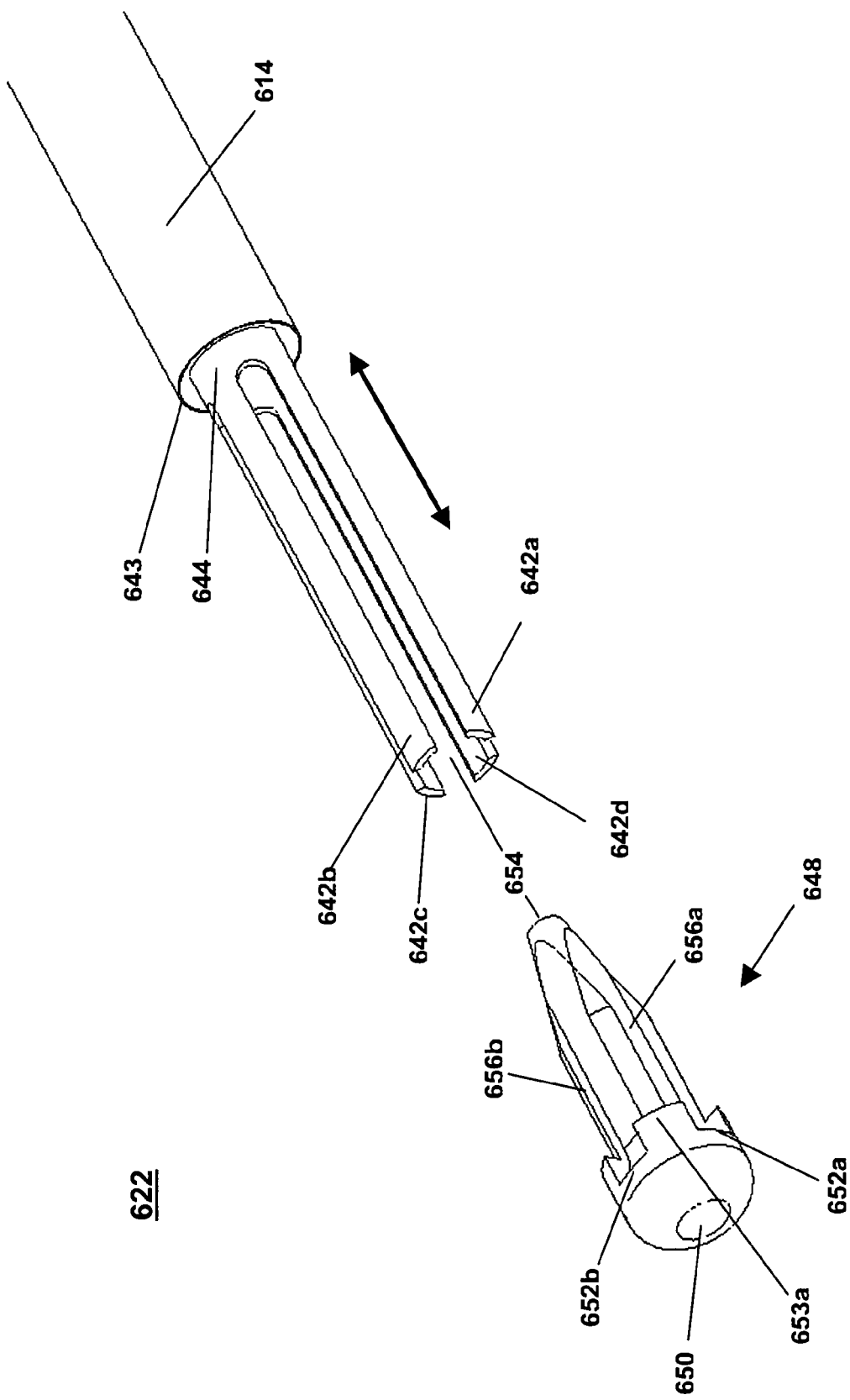
FIG. 9 is an exploded perspective cutaway view of a distal portion of a bone curette constructed in accordance with the principles of the present disclosure.

As shown in FIG. 9, curette 622 includes a tubular body/pusher/cutter 644 within the outer tube 614, and an end cap 648. The other end (not shown) of outer tube 614 includes a plastic molded handle with snapping features to lock and release from bone drill 410. Inside outer tube 614 is pusher/cutting tube 644 having its end cut as shown to create a plurality (four, 4) cutting tines, blades or the like, 642a, 642b, 642c, and 642d. An end cap 648 having conical body 654 and a ball top 650, has four slots or openings 652a, 652b, 652c, and 652d. It is rigidly affixed to the distal end of outer tube 614. The four tines 642a, 642b, 642c, and 642d line up with slots 652a, 652b, 652c, and 652d. The four (4) holes or openings 652a, 652b, 652c, and 652d allow curette blades 642 to be pushed out from outer tube 614 through holes 652. Pusher 644 controls the extension of curette blades 642. Configured guides 656a, 656b, 656c, and 656d of end cap 648 aid in directing blades 642. The tubular shaft assembly is inserted into bone drill 410 with the bone drill causing the blades to turn and create/enlarge a cavity in the targeted bone. It is contemplated that the bone drill 410 may have a variable speed control and may also have a control allowing forward/reverse rotation.

The other end of tube 614, extending from the handle of the outer tube, is molded to interface with the outer tube handle in such a way to allow the user to force inner tube/cutter 644 toward distal end 643 of outer tube 614. As the inner tube is forced distally (axially), tines 642 slide through grooves 652 of tip 650 of end cap 648 and out of outer tube 614 directed by the shape of the slots to project tines 642 in the radial direction. The ends of the tines act as cutting edges to create a cavity.

The user extends tines 642 a short distance (see, e.g. FIG. 11), turns on bone drill 410 and then moves the drill axially through the sheath to enlarge the cavity. As the tines are moved outward (see, e.g. FIG. 12), the drill is moved axially again to enlarge the cavity (see, e.g. FIG. 13) until the cavity is the desired size. The ends of tines 642 may be flat, as shown, or other shapes. Tines 642 are thin in the dimension that is forced to bend by the slots and wider in the dimension that resists deflection during the cutting action. Nitinol may be used as the tine material.

As represented by the double-headed arrows shown in FIG. 9, cutting tube 644 is axially movable relative to tube 614. In this manner, through axial adjustment of cutting tube 644 relative to tube 614, the length of the cutting blades that extend from slots or openings 652a, 652b, 652c, and 652d in the tip 650 of end cap 648 are adjusted and/or controlled. Moreover, in this manner, through radial movement or rotation of outer tube 614 it causes radial movement or rotation of cutting tube 644, cutting tines 642 are radially rotated to cut as desired. Sides and tips of tines 642 are shaped to provide edges or blades as appropriate. These may also include serrations. The serrations may comprise one or more configurations as appropriate for the material to be cut.

Figure 10:
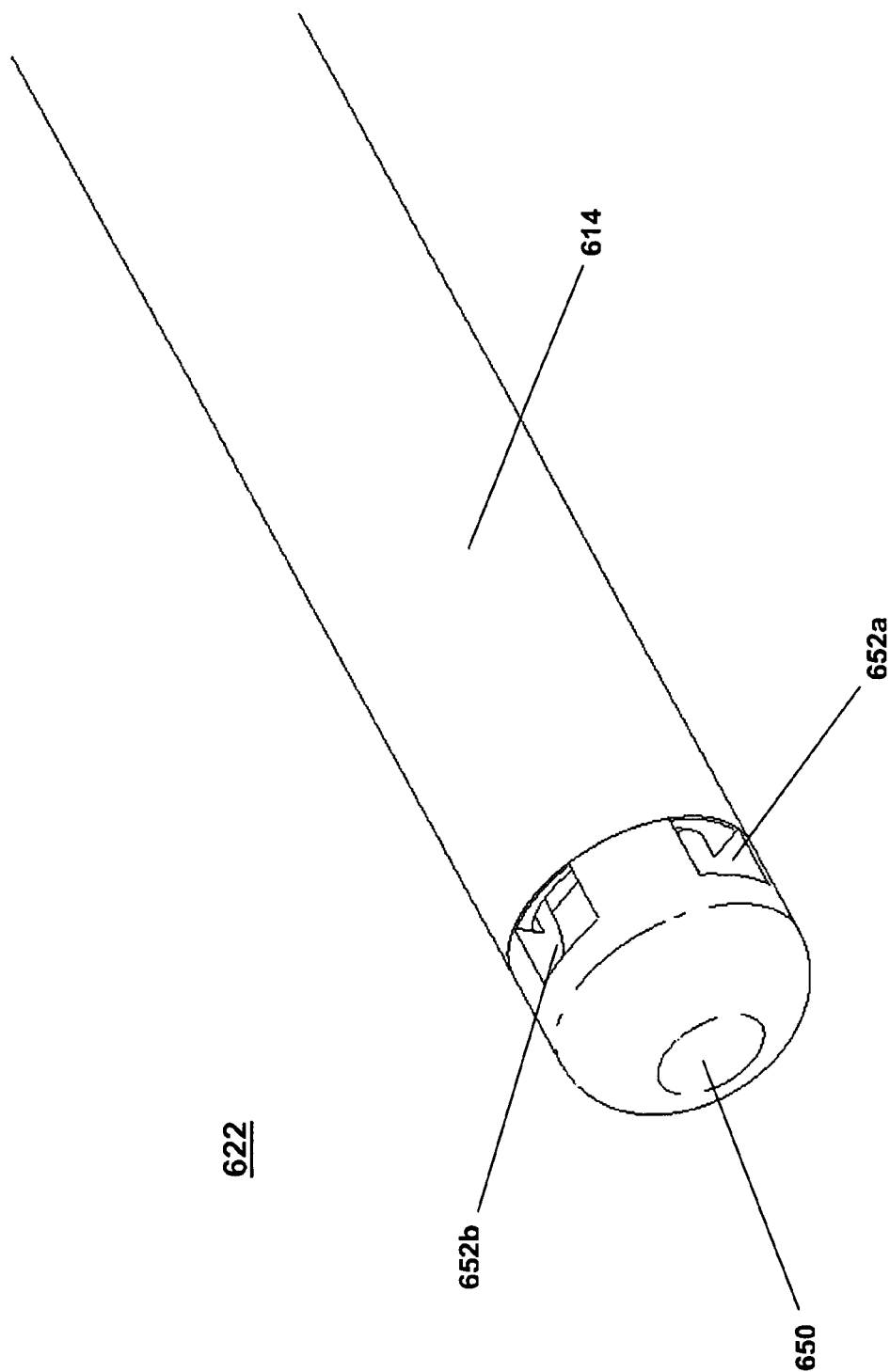
FIG. 10 is a perspective view of the curette shown in FIG. 9 in a retracted position.

FIG. 10 shows curette 622 with four cutting tines 642a, 642b, 642c, and 642d fully retracted into tip 650/tube 614. In this position, curette 622 may be fed through the sheath 56.

Figure 11:
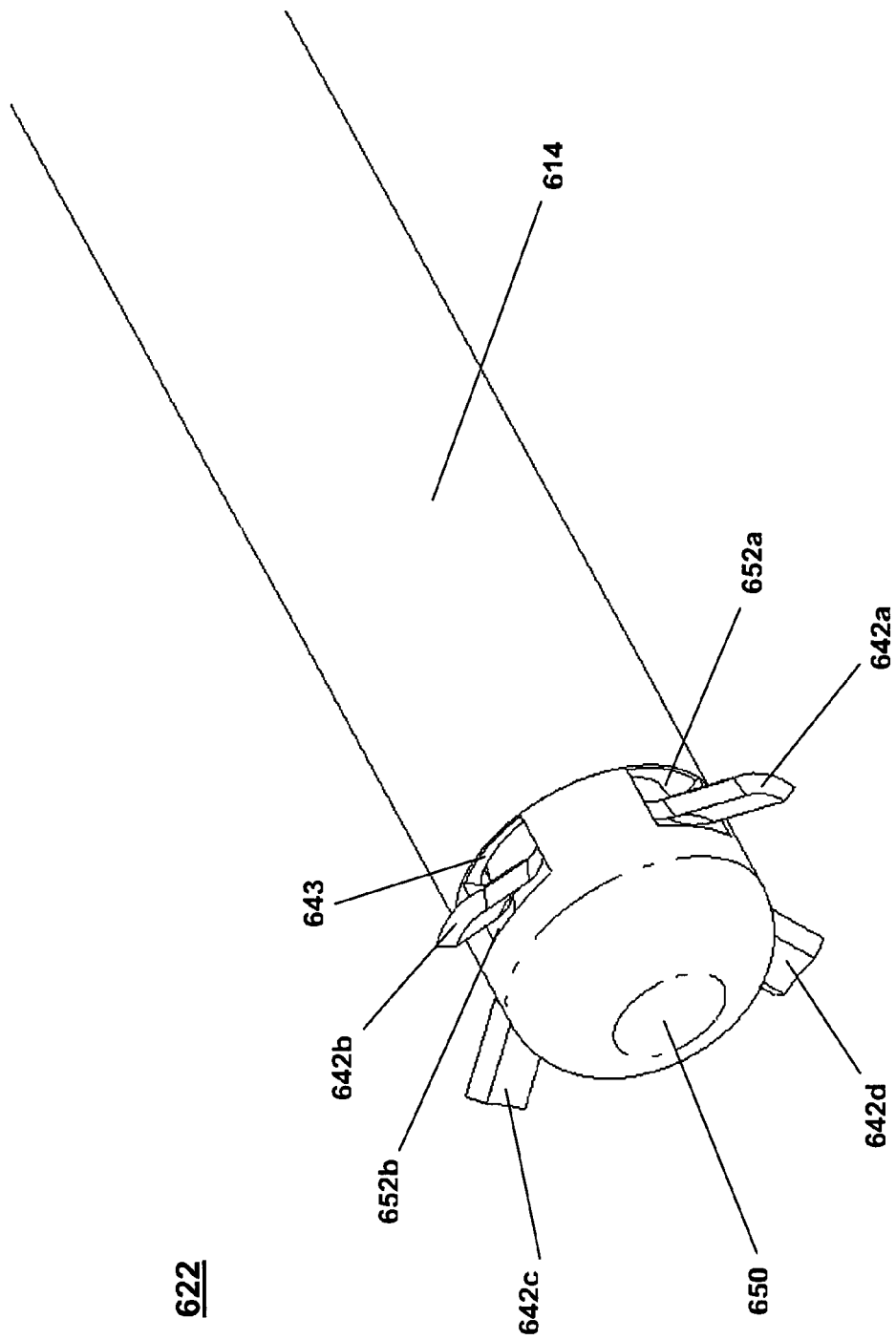
FIG. 11 is a perspective view of the curette shown in FIG. 9 in a minimally extended position.

FIG. 11 shows curette 622 with four cutting tines 642a, 642b, 642c, and 642d in a minimally extended position from tip 650/tube 614. In this position, blades 642a, 642b, 642c, and 642d cut a minimal diameter swath during rotation thereof.

Figure 12:
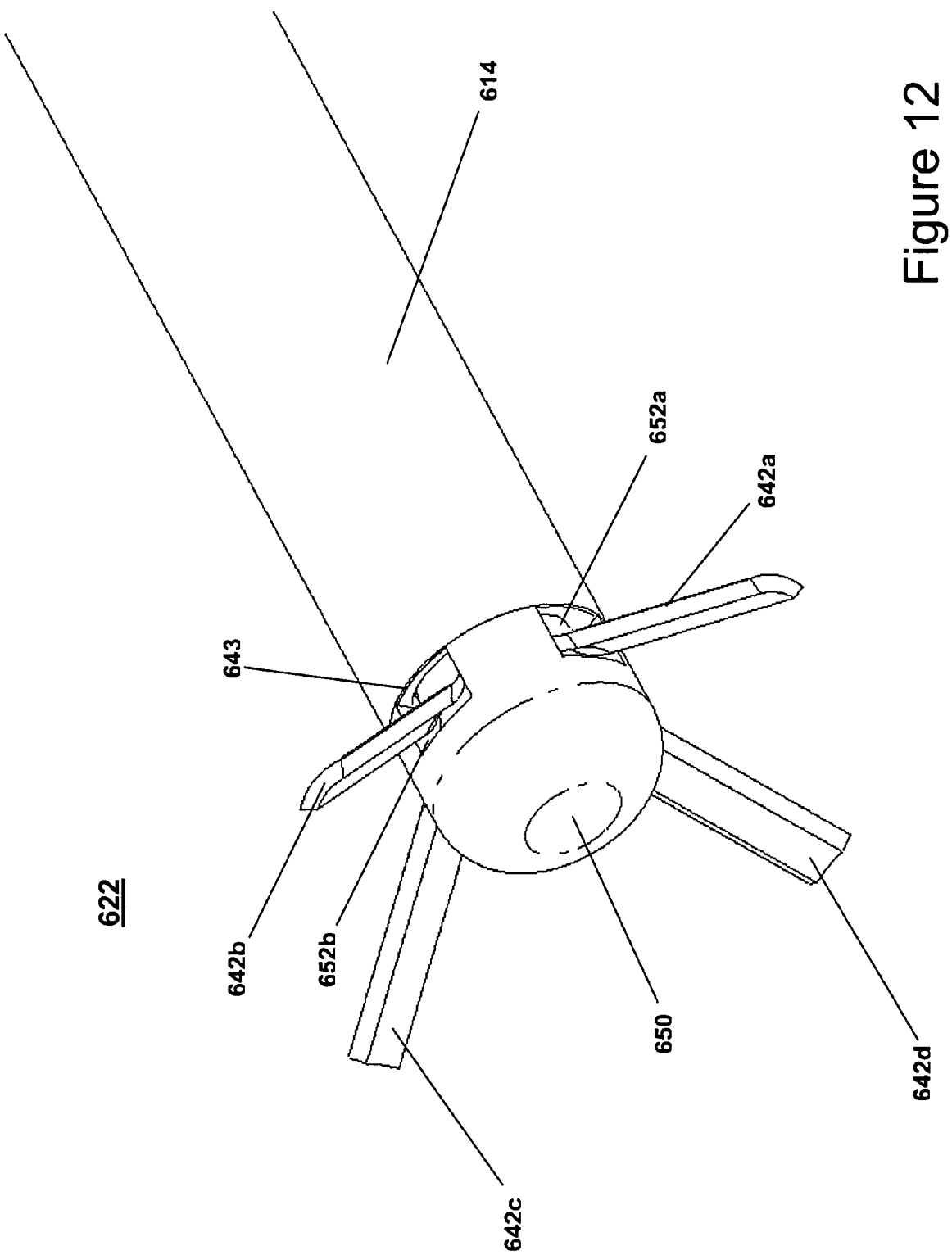
FIG. 12 is a perspective view of the curette shown in FIG. 9, in an intermediately extended position.

FIG. 12 shows curette 622 with four cutting tines 642a, 642b, 642c, and 642d in an intermediately extended position from tip 650. In this position, blades 642a, 642b, 642c, and 642d cut an intermediate diameter swath.

Figure 13:
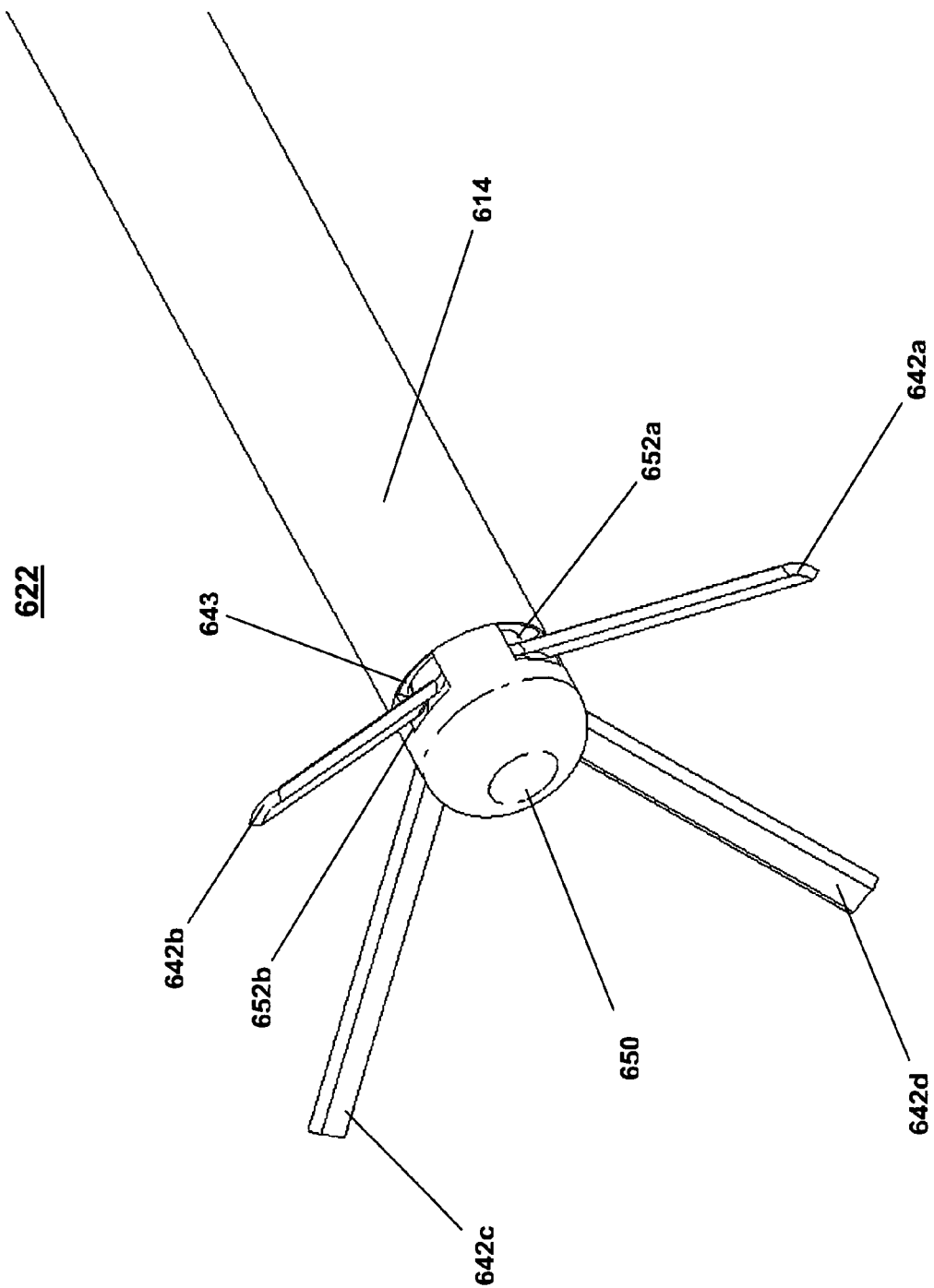
FIG. 13 is a perspective view of the curette shown in FIG. 9 in a maximally extended position.
Figure 14:
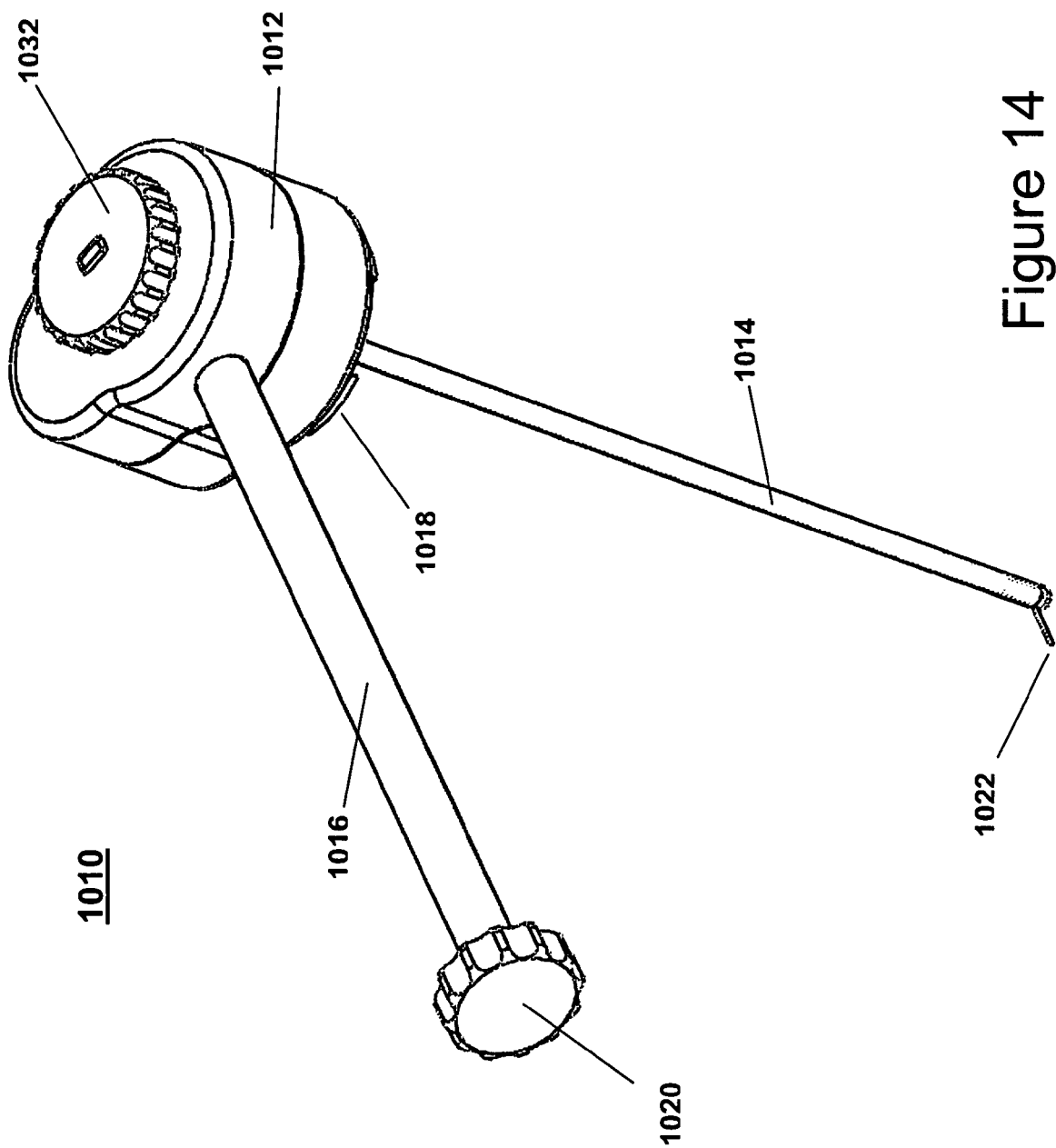
FIG. 14 is a perspective view of an alternate embodiment of the cavity drill constructed in accordance with the principles of the present disclosure.
Figure 15:
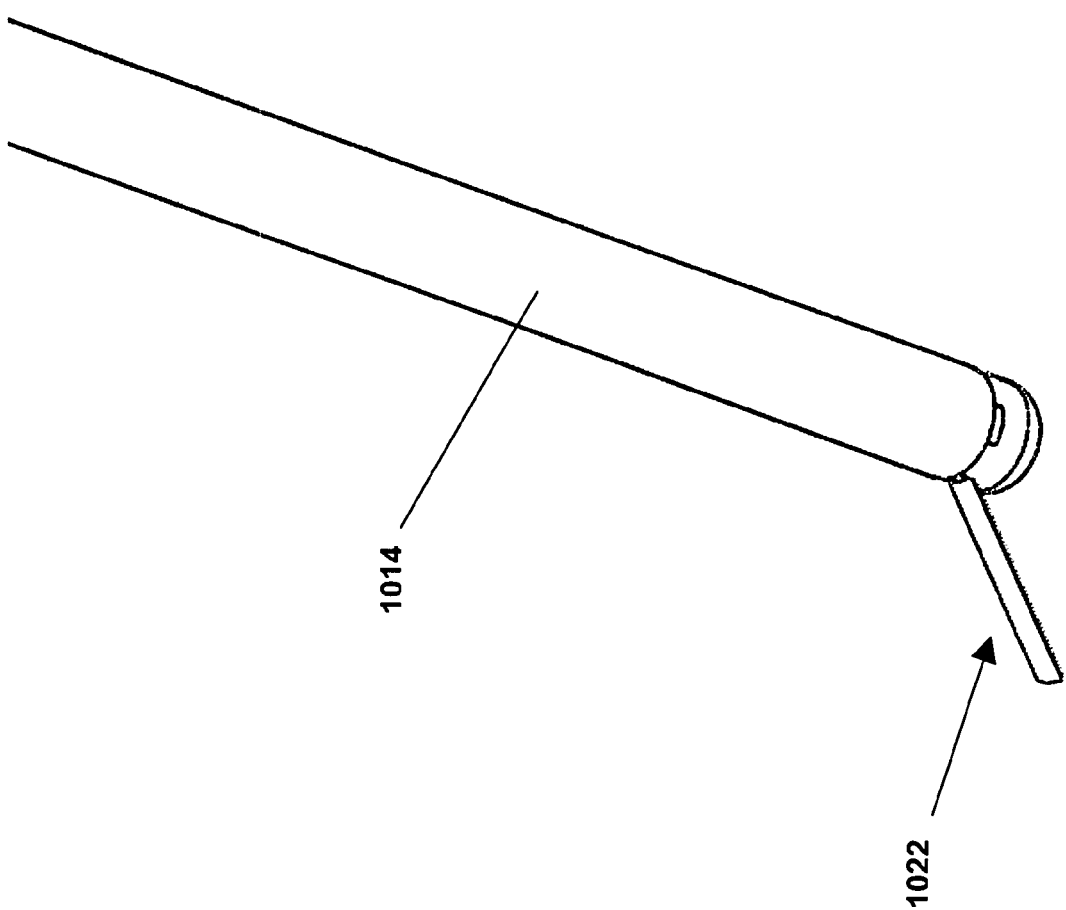
FIG. 15 is a perspective view of an alternate embodiment of a bone curette constructed in accordance with the principles of the present disclosure.
Figure 16:
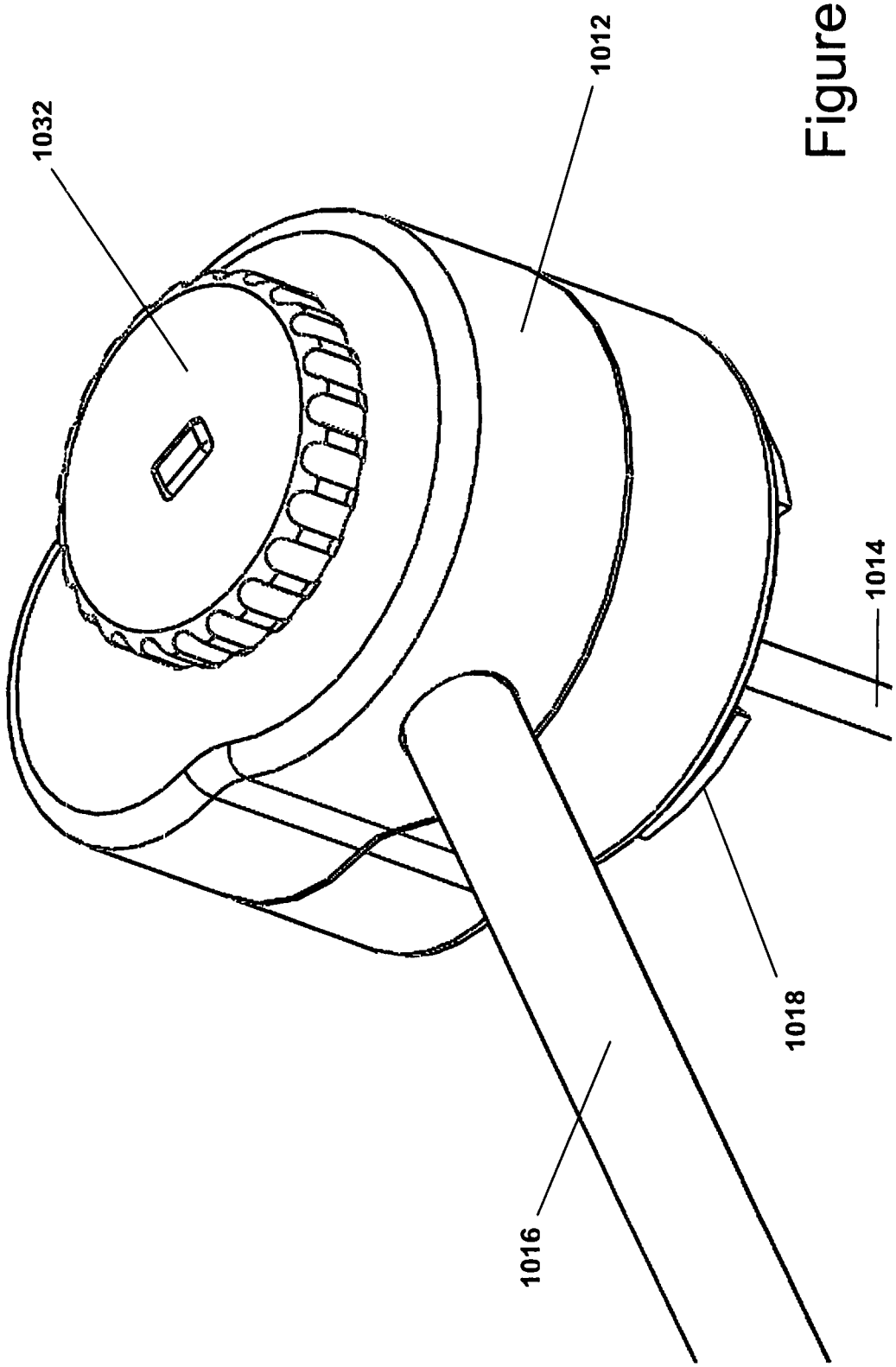
FIG. 16 is an enlarged top perspective cutaway view of the cavity drill shown in FIG. 14.
Figure 17:
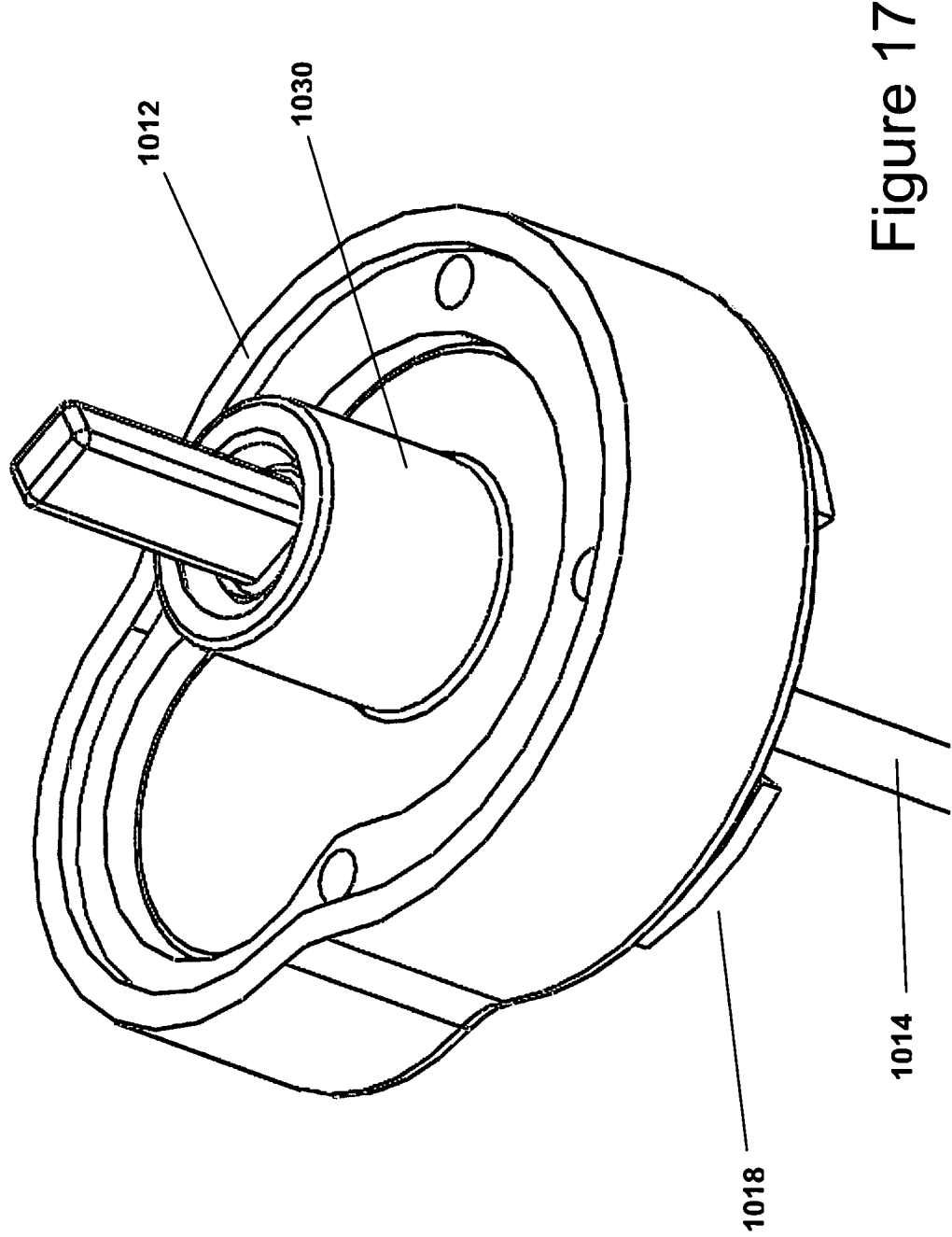
FIG. 17 is an enlarged top perspective view of the cavity drill shown in FIG. 14 with a body portion removed.

FIG. 13 shows curette 622 with four cutting tines 642a, 642b, 642c, and 642d fully extended from tip 650. In this position, a maximum cutting diameter (maximum diameter swath) is achieved during rotation of cutting tube 614/tip650. It should be appreciated that blades 642a, 642b, 642c, and 642d are continuously extendable from the position shown in FIG. 10 through the position of FIG. 13.

Bone drill 410, including cavity drill 610, may include a guard configured to protect a user's hand from radiation. It is contemplated that the guard can be integral to bone drill 410 or alternatively detachable.

Referring to FIGS. 14-21, in an alternate embodiment, bone drill 410 includes a cavity drill 1010, similar to cavity drill 610 described above. Cavity drill 1010 includes a body 1012, a sheath 1014 and a handle 1016. Cavity drill 1010 is assembled by removing the drill bit handle and the sheath 457 of bone drill 410 and attaching cavity drill 1010 thereafter. Body 1012 mounts to head 418 via tabs 1018, which are snapped or inserted with corresponding slots of head 418. Upon attachment, sheath 1014 extends through the support of bone drill 410. Cavity drill 1010 is mounted for rotation relative to head 418. Handle 1016 extends laterally from body 1012 to a knob 1020.

Cavity drill 1010 is similar to cavity drill 610 with respect to the cutter blades being extended and retracted through manipulation of knob 1032 directly, or knob 1020 remotely using the same bevel gear set, male and female internal gears, and the support cylinder. The difference described in this embodiment relates to the method for rotating sheath 1014. For example, sheath 614 in the previous embodiment rotated continuously in one direction or the other, this embodiment creates an oscillation motion through a defined arc for a cutter assembly 1022 that has only one cutter blade. This allows the formation of an asymmetric cavity. As the rotating blades sweep out a cavity defined by the arc of the oscillation, the entire drill assembly can be rotated around to effectively increase the described arc as desired to create an asymmetric cavity as needed.

A motor assembly and output shaft for bone drill 410 is operatively coupled to a gearing assembly of cavity drill 1010 to cause an oscillating rotation of shaft 1014. The gearing assembly is operatively coupled to output shaft 1014 for rotation thereof to perform a cavity creation procedure, similar to those described herein. The gearing assembly of cavity drill 1010 is disposed with body 1012 and includes a wheel gear 1042 operatively coupled to support cylinder 514 (defined previously). This configuration translates rotation of the motor/gearhead assembly through the support cylinder to rotation of wheel gear 1042.

Wheel gear 1042 engages/meshes with a pinion gear 1044 causing corresponding rotation thereof. A cylinder 1046 is mounted with pinion gear 1044 and simultaneously rotates therewith. A connecting link 1048 is mounted to cylinder 1046 and drive link 1054. Connecting link 1048 has a first end 1050 attached to cylinder 1046 and a second end 1052 attached to drive link 1054 which is mounted about output shaft 1014. This configuration advantageously provides an asymmetric volume center around output shaft 1014, which oscillates bone curette 1022 back and forth as an alternative to rotating continuously in one direction.

Figure 18:
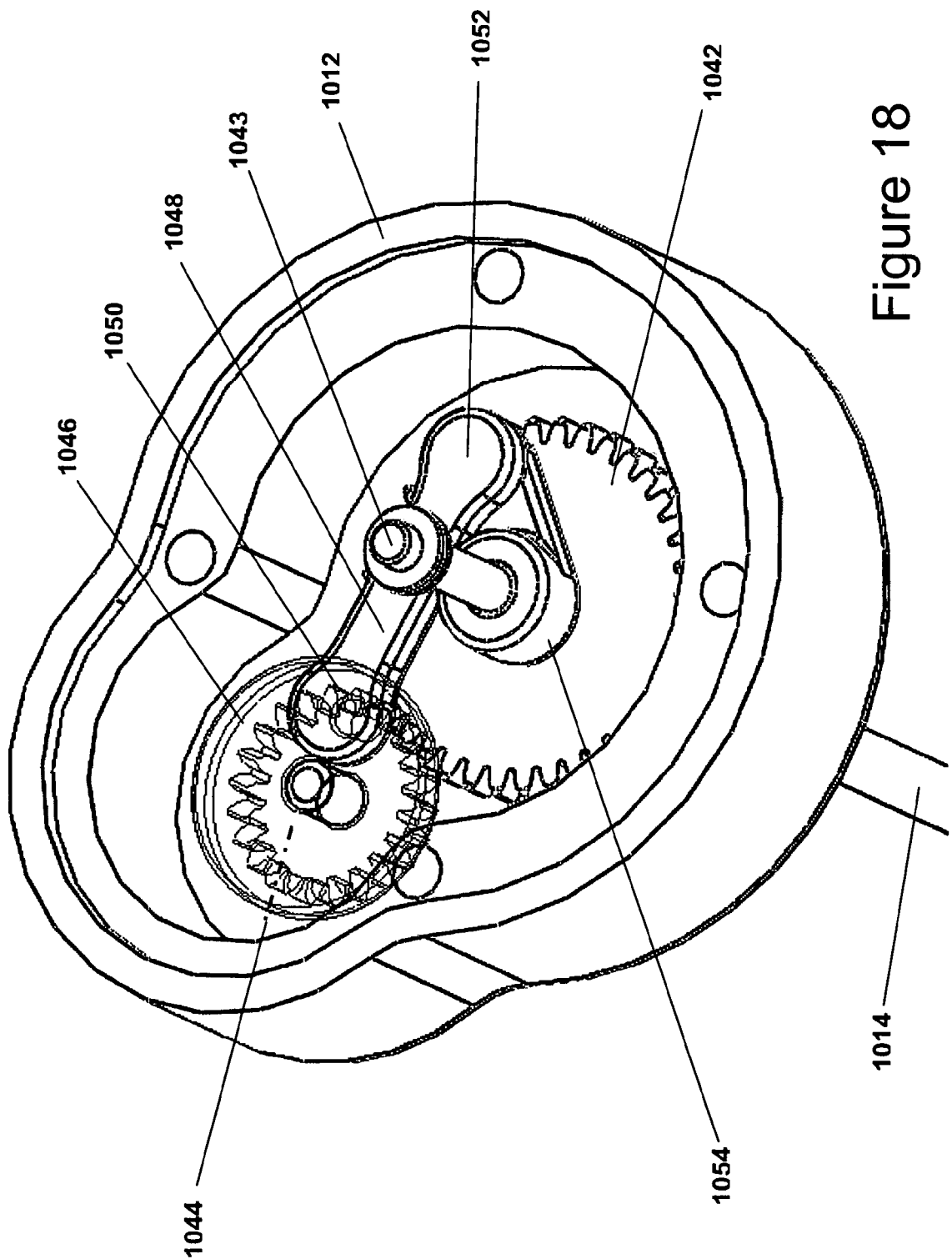
FIG. 18 is an enlarged top perspective view of the cavity drill shown in FIG. 14 with parts removed.

As shown in FIG. 18, second end 1052 is in a downward position, relative to the perspective view of the Figure. As cylinder 1046 is caused to rotate, as discussed above, in for example, a counter clockwise direction, first end 1050 rotates about the center of pinion gear 1046. Rotation of first end 1050 translates motion of link 1048, which causes second end 1052 to move from the downward position to an upward position, as shown by arrow A in FIG. 20.

Figure 19:
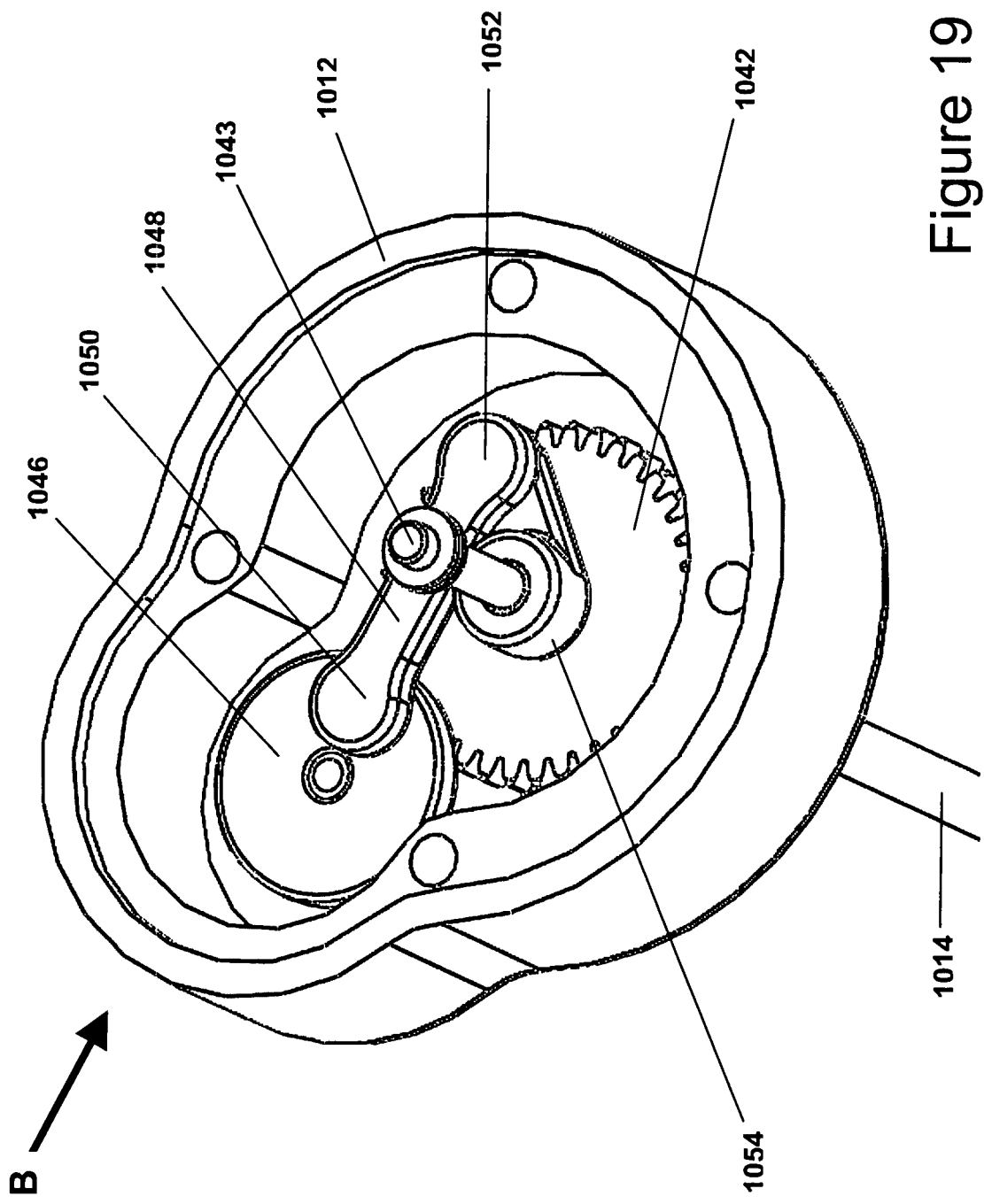
FIG. 19 is an enlarged top perspective view of the cavity drill shown in FIG. 14 with parts removed.
Figure 20:
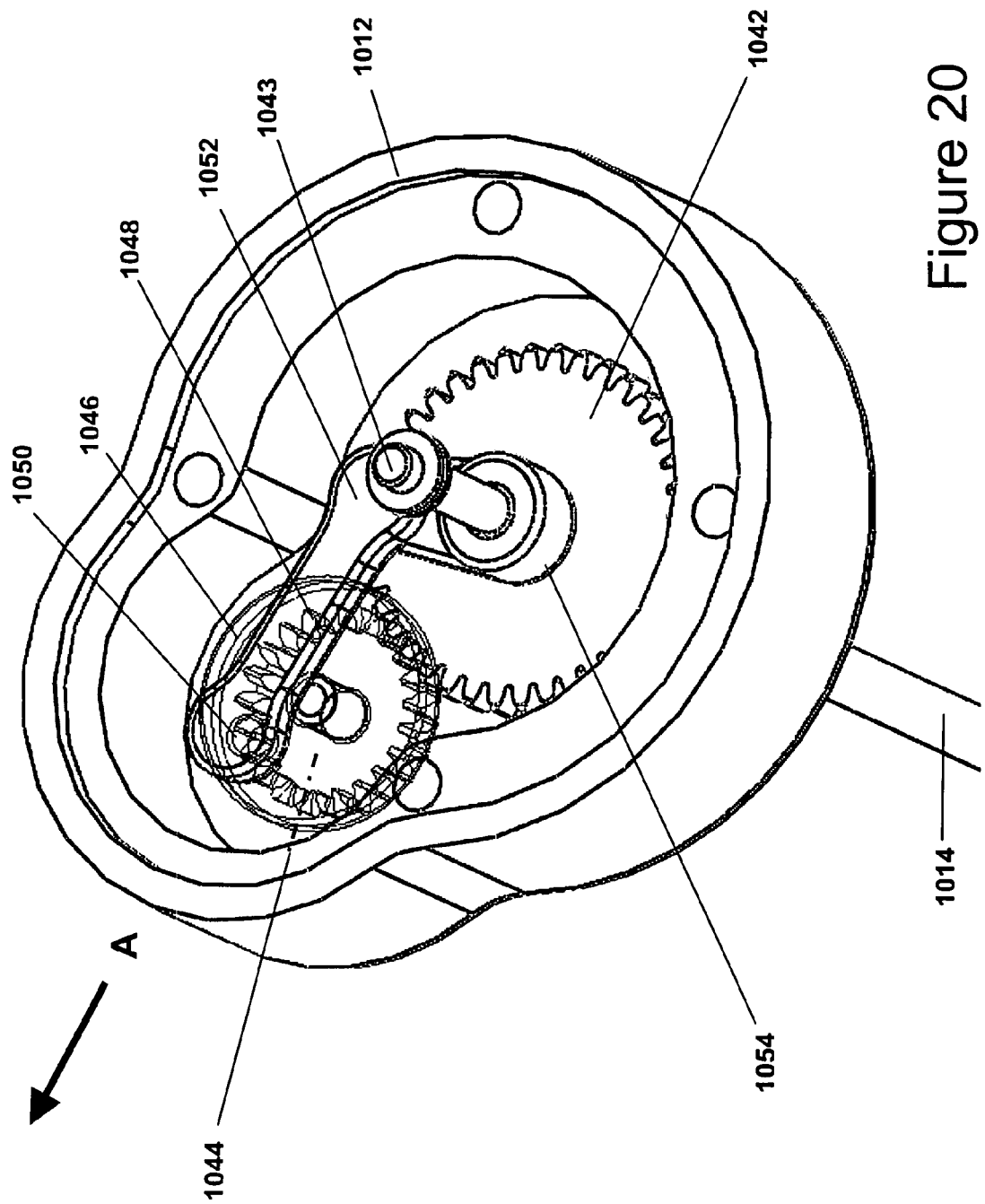
FIG. 20 is an enlarged top perspective view of the cavity drill shown in FIG. 14 with parts removed.
Figure 21:
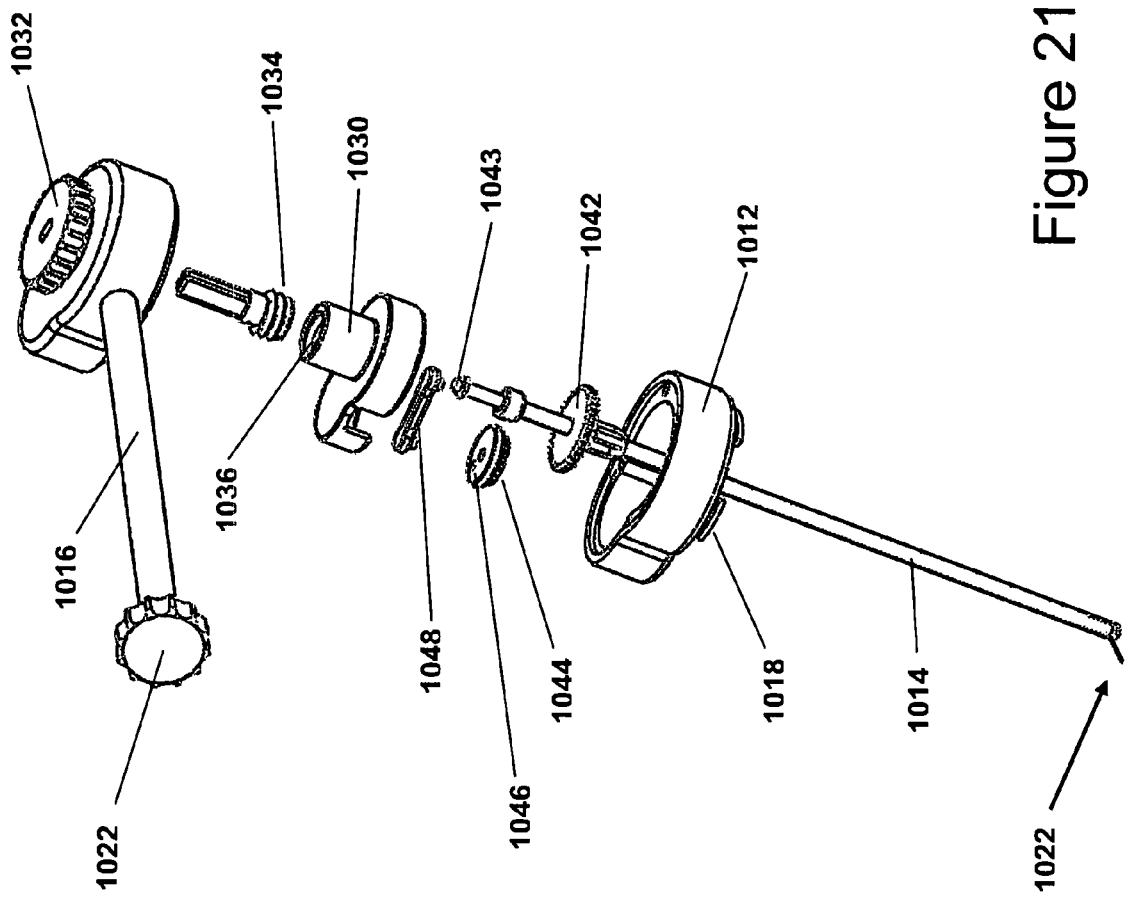
FIG. 21 is a perspective view of the cavity drill shown in FIG. 14 with parts separated in an exploded view.
Figure 22:
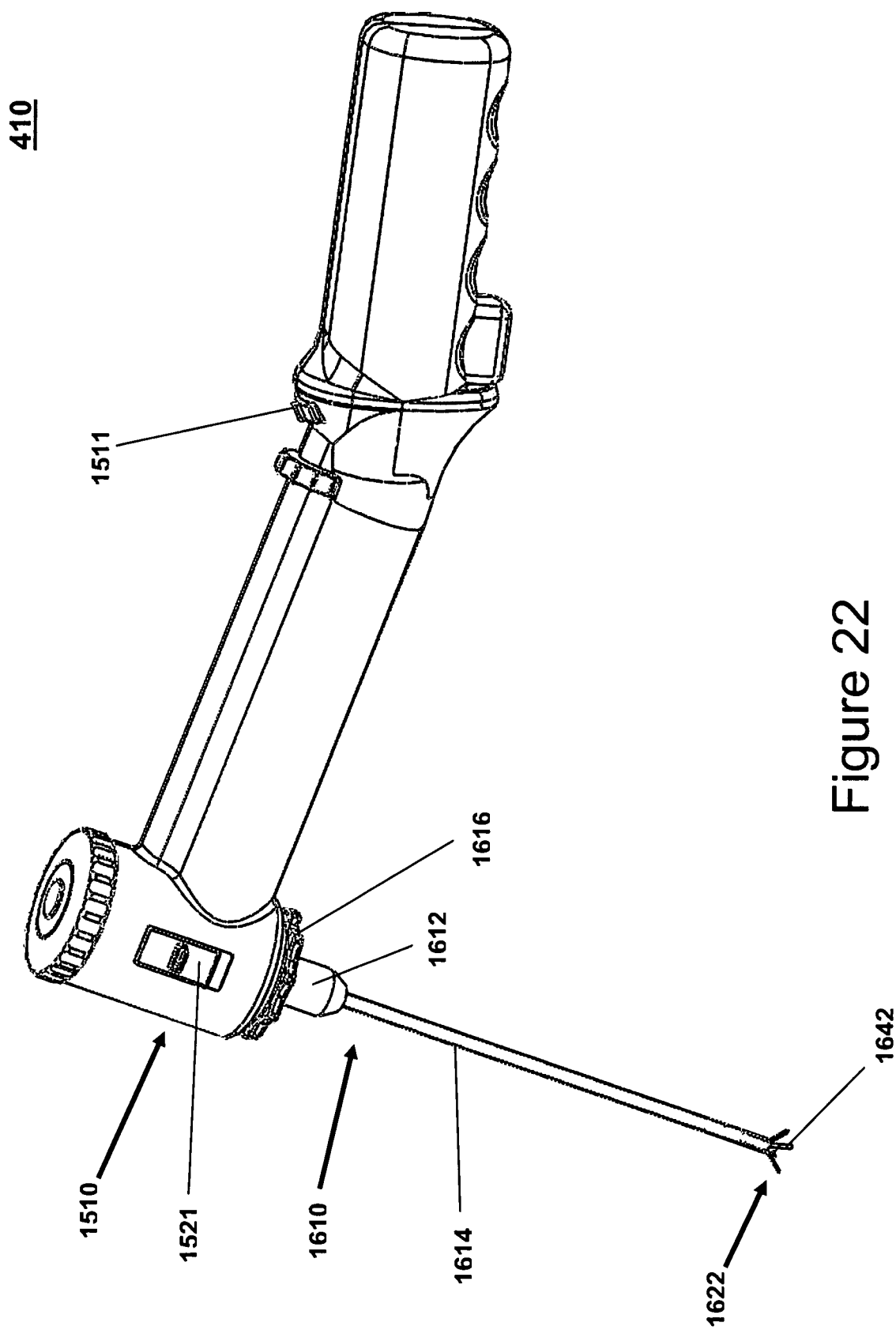
FIG. 22 is a side perspective view of an alternate embodiment of the bone drill shown in FIG. 1 constructed in accordance with the principles of the present invention.

As first end 1050 continues in a counter-clockwise direction about the center of pinion gear 1046, motion of link 1048 causes second end 1052 to move from the upward position to the downward position, as shown by arrow B in FIG. 19. This advantageous design converts the continuous rotation of the output shaft and motor assembly of bone drill 410, to an oscillating motion of bone curette 1022 during a cavity creation procedure. By eliminating all but one of the cutting blades, this design can now cut an asymmetric volume in the vertebral body. The user would extend the single blade and excise a defined arc, for example, about 60 degrees. The user then rotates bone drill 410 (or possibly the cavity drill body only) to excise a different area around output shaft 1014. This design is useful, for example, if the access hole into a vertebral body is too close to an outside wall or a top/bottom plate.

Figure 23:
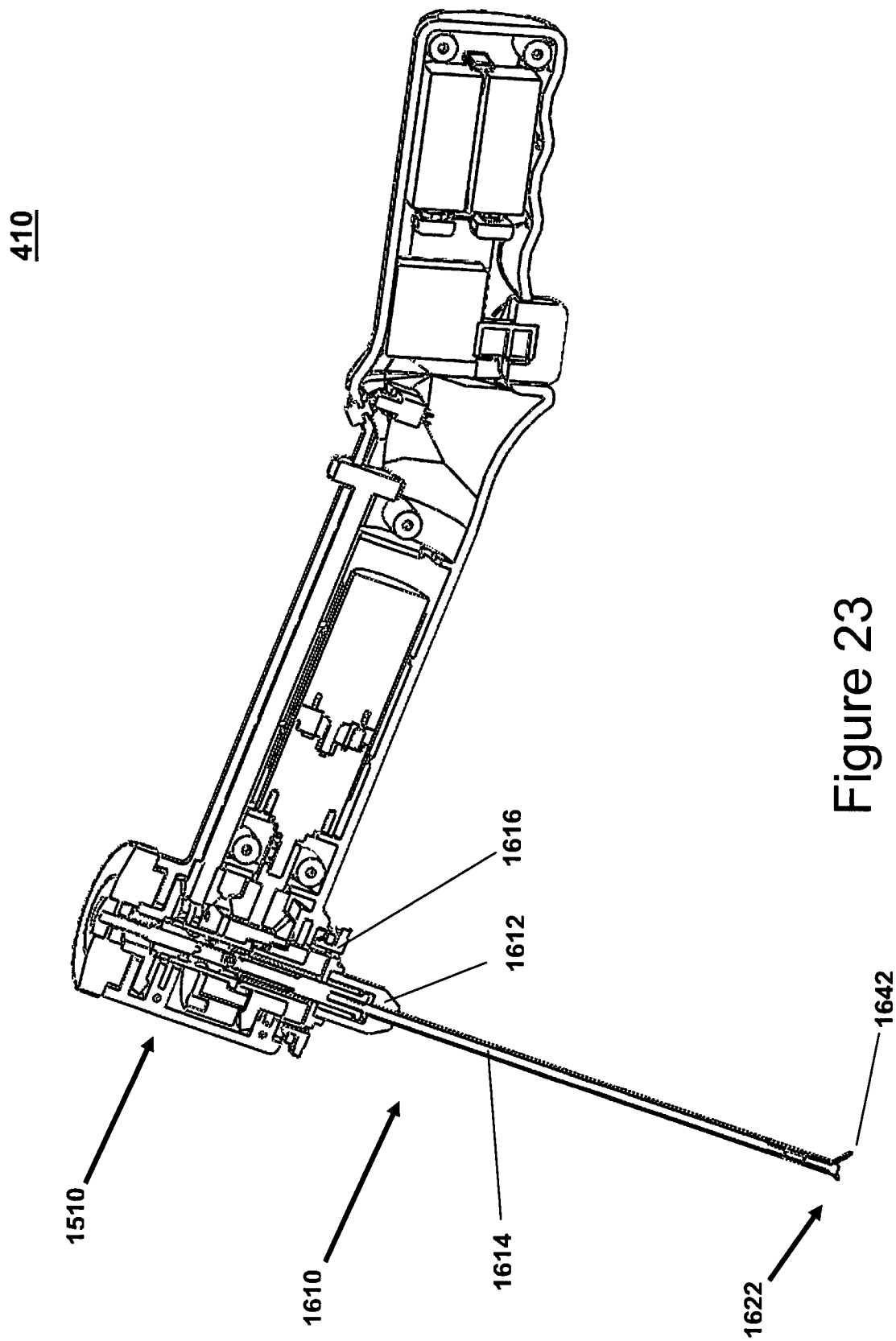
FIG. 23 is a side perspective sectional view with cover removed of the bone drill shown in FIG. 22.
Figure 24:
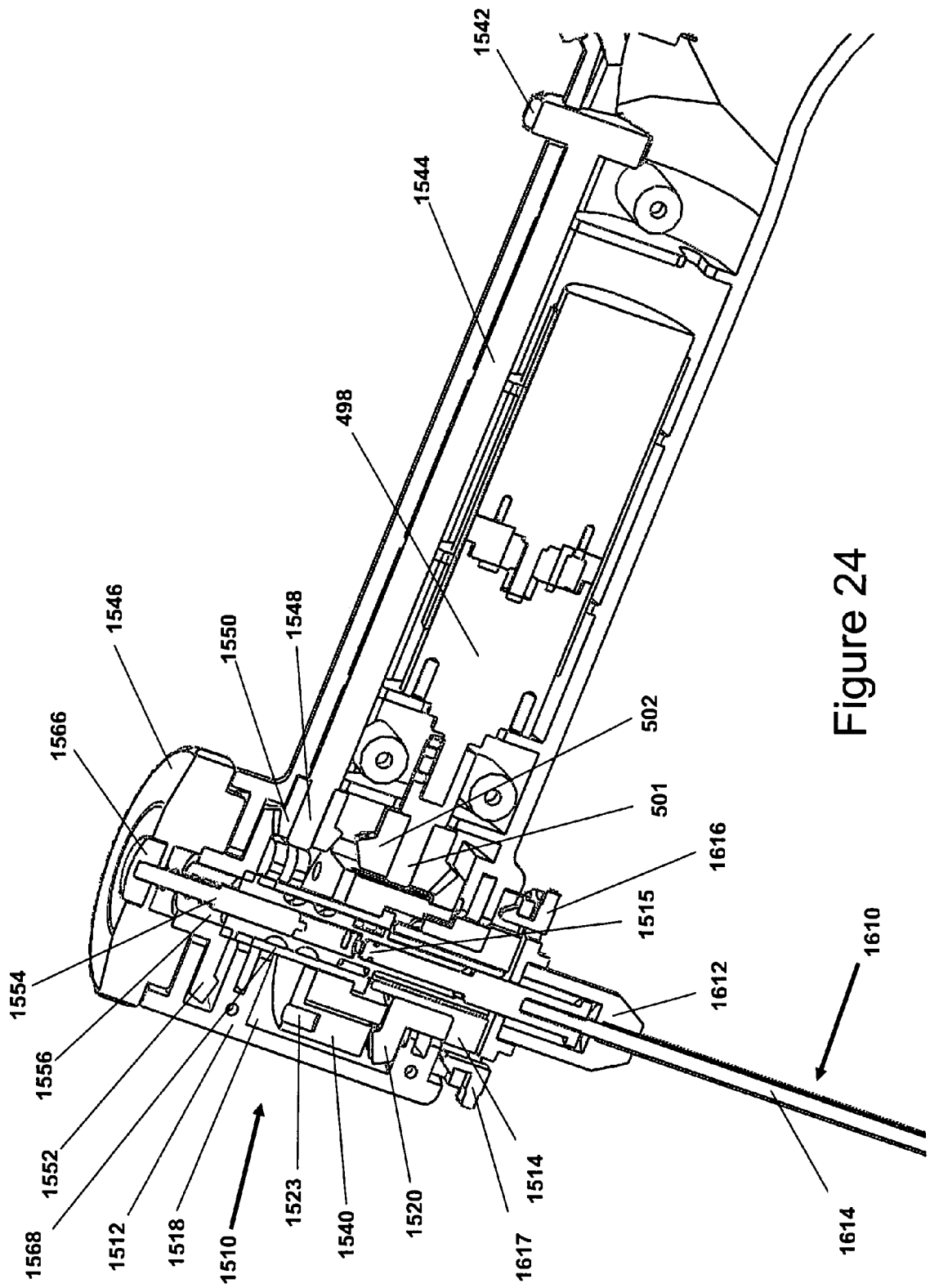
FIG. 24 is an enlarged side perspective view, in cross section of the head portion shown in FIG. 22.
Figure 25:
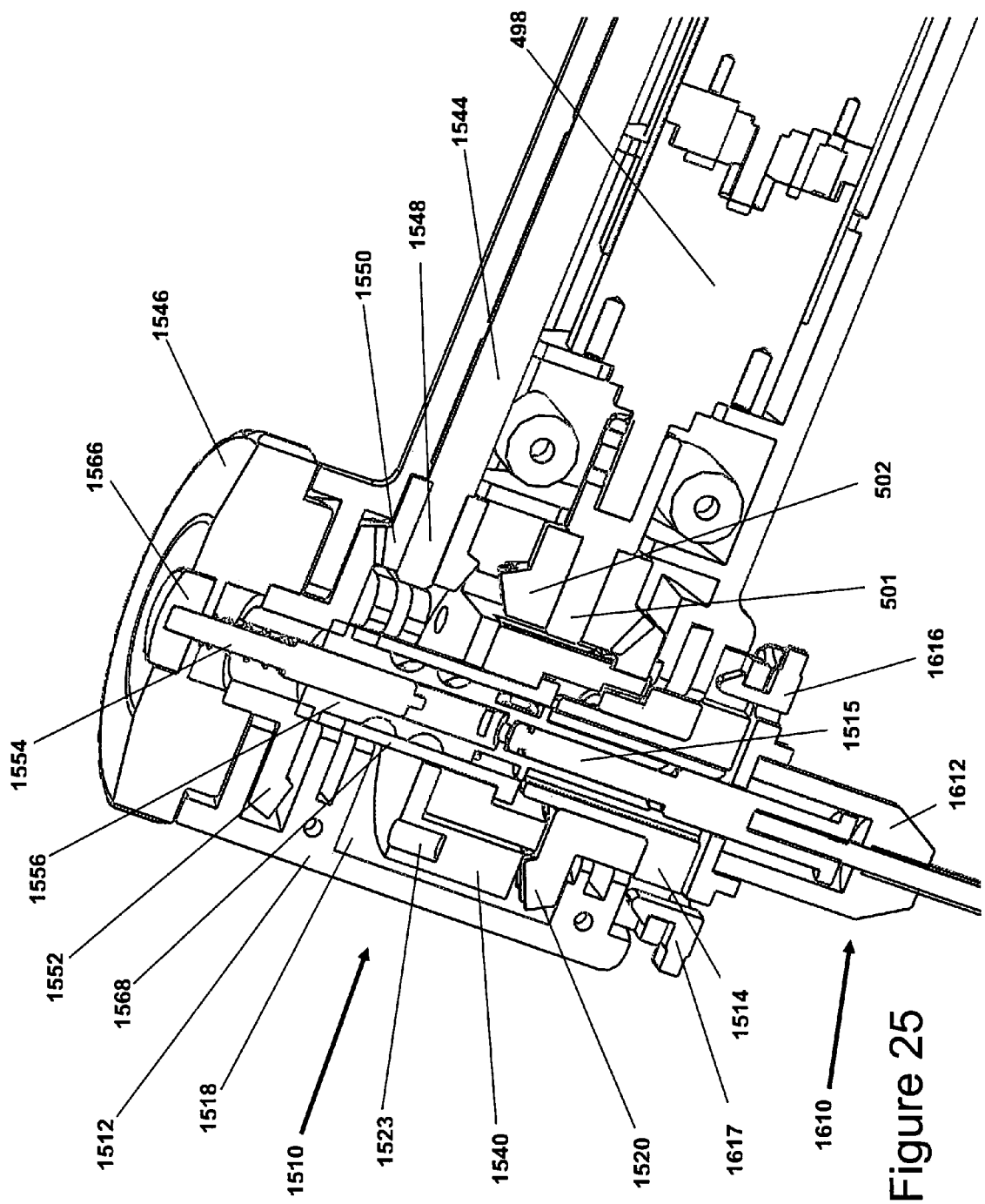
FIG. 25 is an enlarged side perspective view, in cross section of the head portion shown in FIG. 22.
Figure 26:
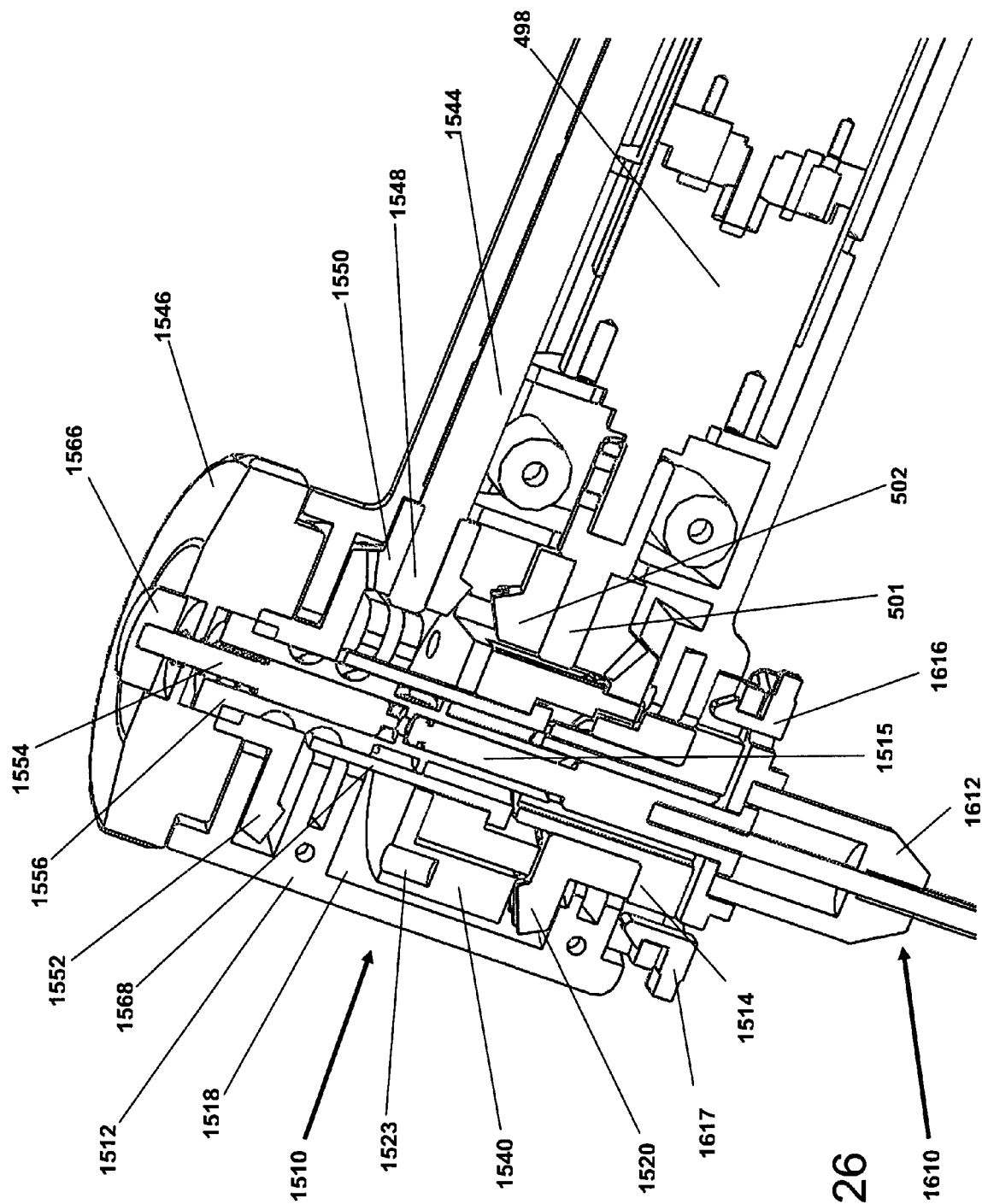
FIG. 26 is an enlarged side perspective view, in cross section of the head portion shown in FIG. 22.
Figure 27:
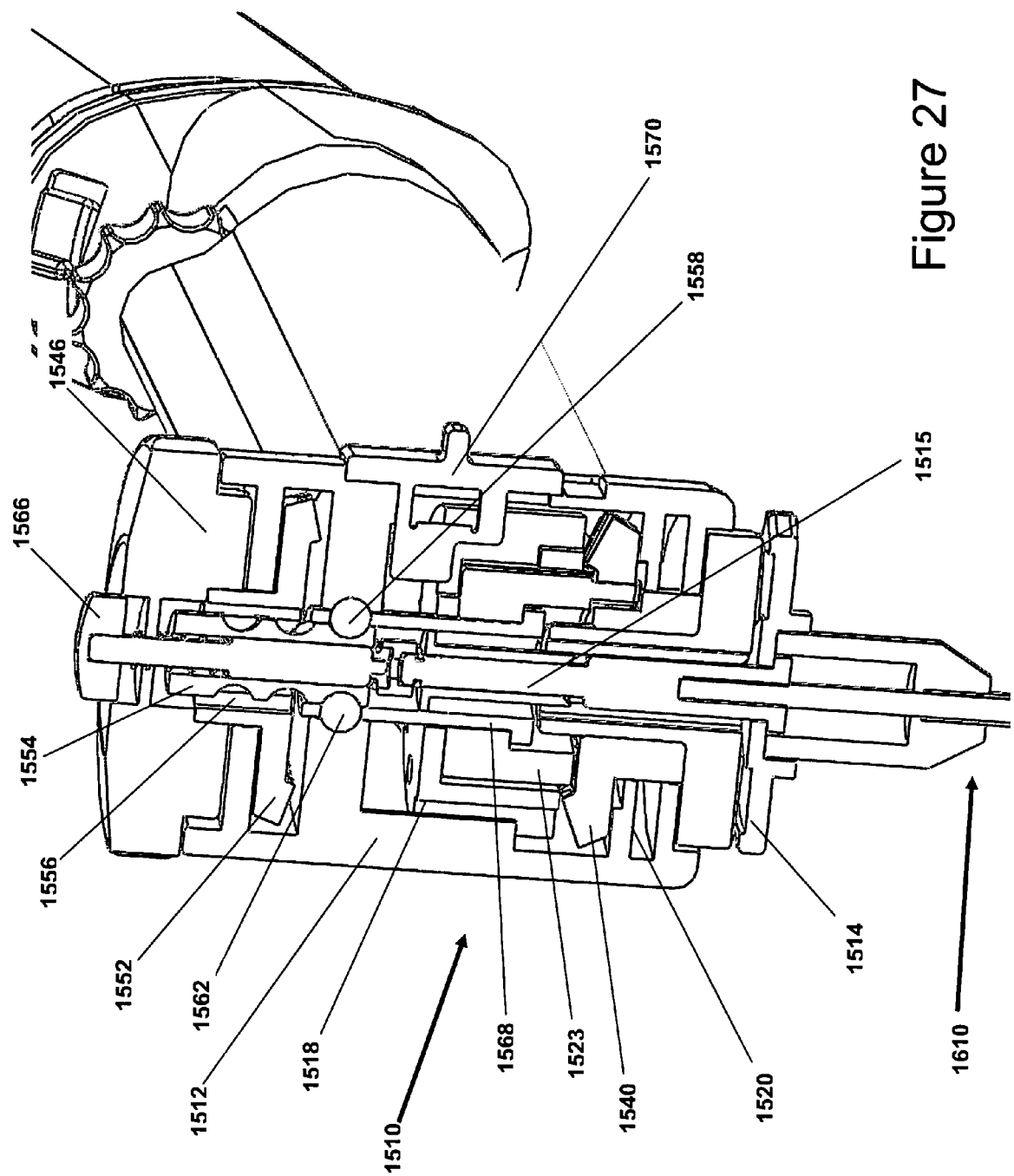
FIG. 27 is an enlarged front perspective view, in cross section of the head portion shown in FIG. 22.
Figure 28:
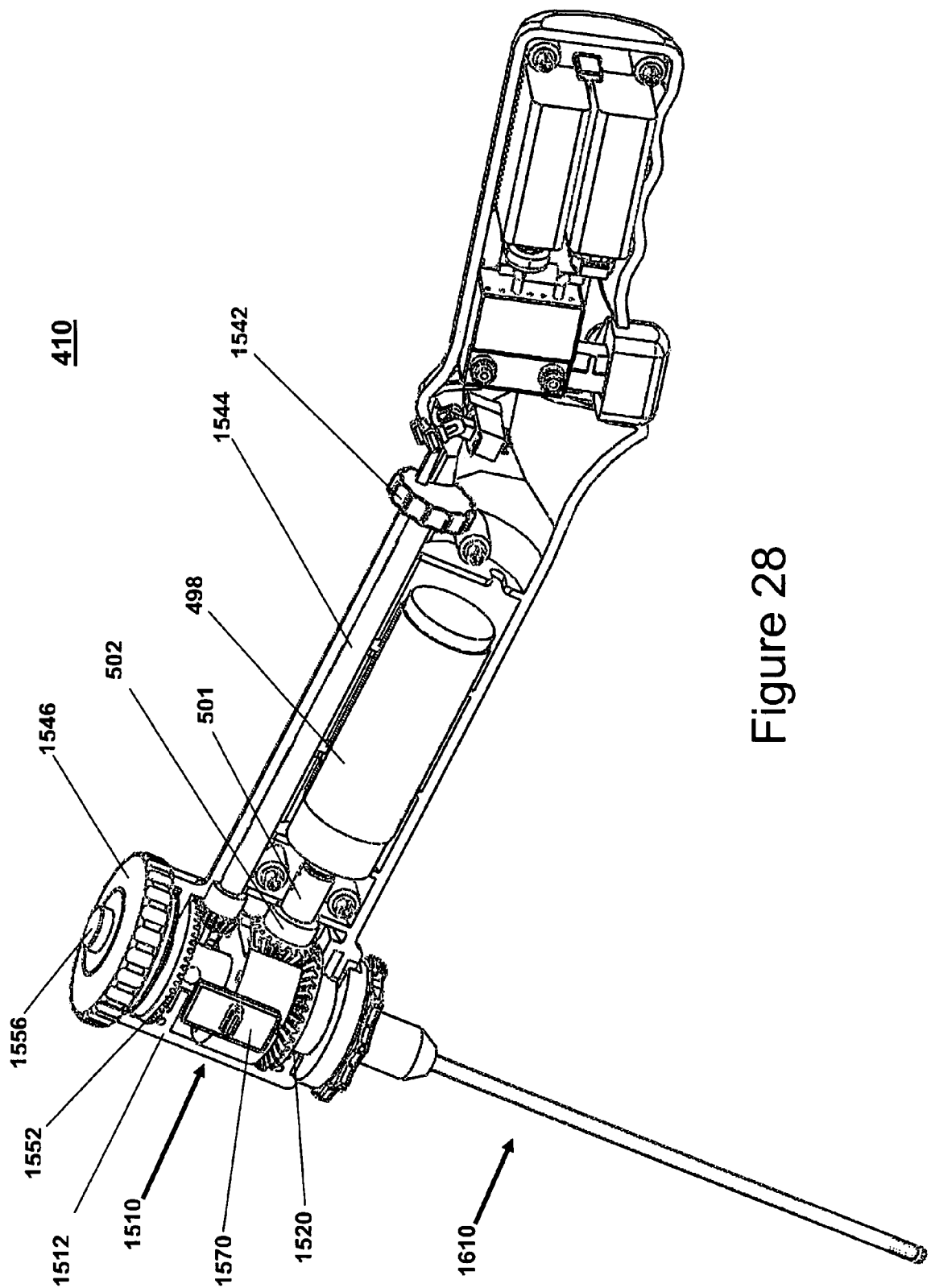
FIG. 28 is a side perspective sectional view with cover removed of the bone drill shown in FIG. 22.
Figure 29:
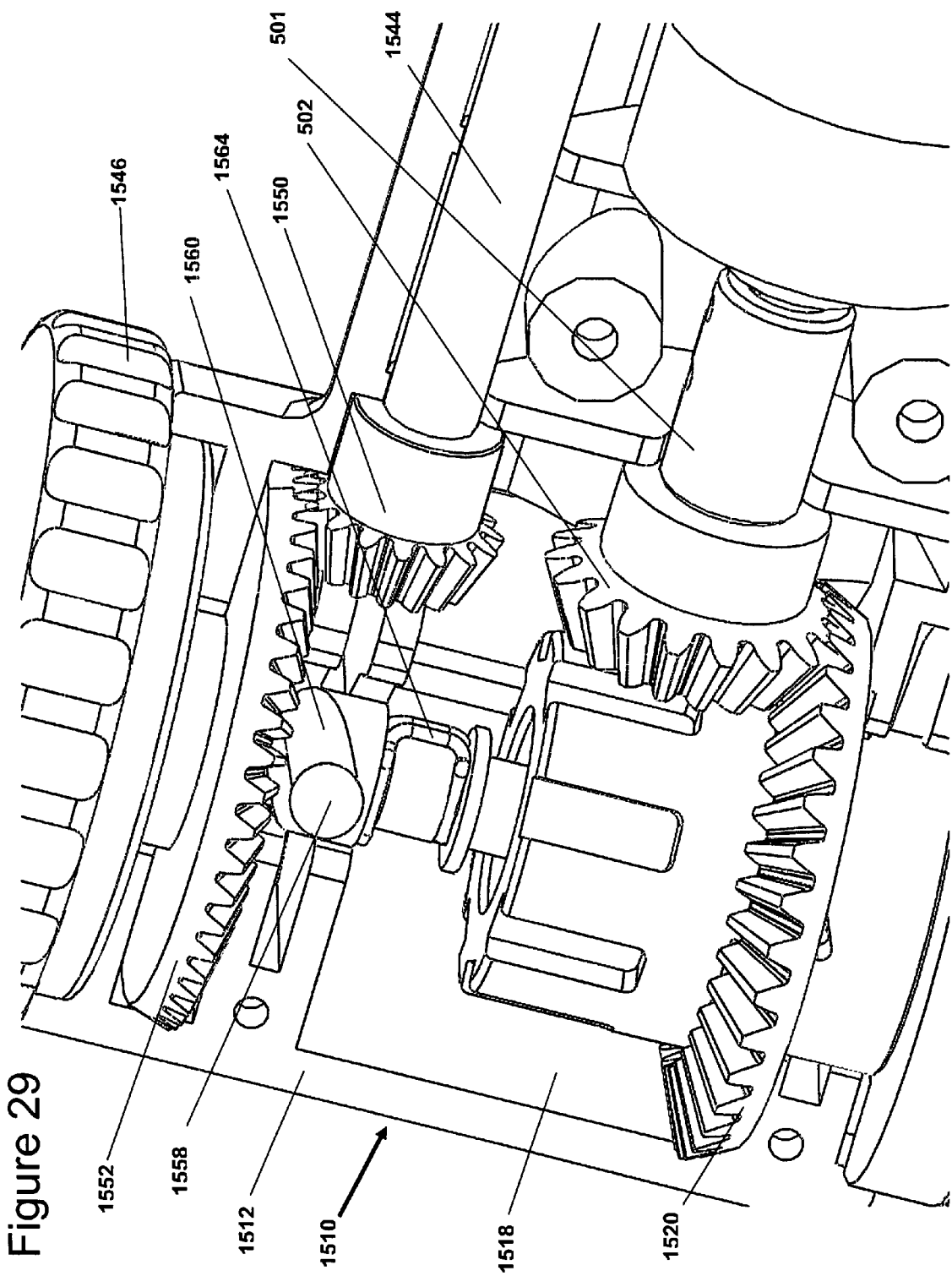
FIG. 29 is a side perspective sectional view with cover removed of the head portion of bone drill shown in FIG. 22.

Referring to FIGS. 22-29, an alternate embodiment of bone drill 410 is shown, similar to that described above, which includes a head portion 1510 and a cavity drill assembly 1610, similar to cavity drill 610 described above and alternatively mounted to bone drill 410, for creating and/or enlarging a cavity in targeted bone. Bone drill 410 includes a forward/reverse switch 1511, which is connected to the power supply, the variable speed trigger switch, and the motor. It is contemplated that bone drill 410 may employ nine volt batteries as a power source, as shown in FIG. 23. It is further contemplated that bone drill 410 may employ various battery or portable power arrangements, AC or DC power sources, etc.

Head portion 1510 has a body 1512 that defines an interior cavity 1518, which supports the cavity drill assembly drive gearing. A motor assembly 498 is operatively coupled to an output shaft 501 for rotation thereof via associated gearing. (See, for example, a description of such assembly in co pending and commonly owned U.S. Utility patent application Ser. No. 11/788,413, filed on Apr. 20, 2007 under Express Mail Label No. ER 550793142 US). A bevel gear 502 is connected to output shaft 501 for meshing/engaging with the cavity drill assembly gearing in head portion 1510.

Bevel gear 502 meshes with an input gear 1520 of the cavity drill assembly gearing. Input gear 1520 is retained with a sheath drive plate 1514 which is connected to cavity drill assembly 1610, as will be described.

Input gear 1520 has radially disposed cams, which are correspondingly configured to engage radially disposed followers of an impact ram 1540, to translate impact energy to targeted bone for creating and/or enlarging a cavity, as will be described. (See, for example, a description of such a cam and follower assembly in co pending and commonly owned U.S. Utility patent application Ser. No. 11/788,413, filed on Apr. 20, 2007 under Express Mail Label No. ER550793142 US).

Impact ram 1540 rotates with input gear 1520. Alternatively, an impact switch 1521 is moved to provide a stop for impact ram 1540 to stop rotation and cause impact ram 1540 to move up and down. Impact ram 1540 includes a ram weight 1523 to increase impact force. Ram weight 1523 has 3 holes configured for supporting compression springs that provide return force.

A knob 1542 extends laterally from body 1512 via a shaft 1544. Knob 1542 is configured to facilitate remote manipulation of a knob 1546 from a distance that allows a user's hands to remain away from the radiation beam while adjusting the sheath extension. Knob 1542 is knurled to facilitate manipulation thereof. Rotating knob 1546 directly, or remotely using knob 1542, causes the components of cavity drill assembly 1610 to extend or retract for creating and/or enlarging a cavity in targeted bone.

Shaft 1544 includes an output shaft 1548, mounted with a bevel gear 1550, which translates rotation of knob 1542 and shaft 1544 to the gearing of body 1512. Bevel gear 1550 meshes with an input gear 1552 of the gearing of body 1512.

Input gear 1552 is mated to knob 1546 through the upper housing of body 1512. Input gear 1552 includes teeth radially disposed thereabout that mesh with teeth of bevel gear 1550. As bevel gear 1550 rotates, as caused by rotation of shaft 1544 described above, input gear 1552 is caused to rotate, which in turn rotates knob 1546.

Knob 1546 is knurled to facilitate manipulation thereof. Knob 1546 is disposed for extension and retraction of the components of cavity drill assembly 1610. Knob 1546 is slidably mounted to push rod 1554. As knob 1546 rotates, a shuttle 1556 rotates, via splines that threadably engage input gear 1552. The sliding splines allow the shuttle 1556 to translate axially relative to gear 1552 as it rotates. Shuttle 1556 is fixed in position along the drive axis of body 1512 by guide balls 1558 that ride in helical grooves 1560 of shuttle 1556. Guide balls 1558 are fixed in position with recesses 1562 of housing 1512. Thus, rotation of shuttle 1556 causes shuttle 1556 to translate up or down due to the threaded engagement of helical grooves 1560 with the fixed guide balls 1558.

Shuttle 1556 locks the proximal end of cavity drill assembly 1610 via a spring wire form 1564 that springs out and then back into a groove on the proximal end of cavity drill assembly 1610. To remove cavity drill assembly 1610, cavity drill assembly 1610 is retracted completely so that push rod 1554 engages spring wire form 1564. An eject button 1566, connected to push rod 1554, is depressed such that push rod 1554 engages and spring wire form 1564 opens, releasing the proximal end of cavity drill assembly 1610.

A slide 1568 translates impact energy from impact ram 1540 to shuttle 1556. Slide 1568 translates the impact energy through guide balls 1558. As impact ram 1540 moves downward, impact ram 1540 engages the flange on slide 1568. Slide 1568 moves downward, pulling guide balls 1558 in the same direction. Guide balls 1558 in turn cause shuttle 1556 to move downward, transferring the impact energy through cavity drill assembly 1610 into the bone.

Cavity drill assembly 1610 includes a body 1612, a sheath 1614 and a flange 1616. Flange 1616 mounts to head portion 1510 via tabs 1617, which are snapped or inserted with corresponding slots of sheath drive plate 1514.

Cavity drill assembly 1610 is powered by motor assembly 498. Activating the motor causes sheath 1614 to rotate, which in turn rotates bone curette 1622, similar to bone curette 622 described above. As bone curette 1622 rotates, blades 1642, stored therewith, rotate and can be extended and retracted for creating and/or enlarging a cavity in targeted bone. Blades 1642 are extended and retracted through the rotation of knob 1546, which causes translation of the shuttle 1556 thereby causing translation of a push rod inside sheath 1614 relative to sheath 1614 forcing the blades out through the openings in the tip, as in the previous embodiment.

While the invention has been illustrated and described in detail in the drawings and foregoing description, the same is to be considered as illustrative and not restrictive in character, it being understood that embodiments have been shown and described and that all changes and modifications that come within the spirit of this invention are desired to be protected.

What is claimed is:

1. A cavity drill configured for use with a bone drill comprising:
    a body configured for releasable coupling to a portion of a bone drill;
    an elongate sheath extending from the body; and
    a cutting tool coupled to a distal portion of the elongate sheath and comprising a plurality of elongate blades adapted for deployment between a retracted position and plurality of extended positions, the retracted position comprising a configuration that is axially disposed within the elongate sheath, each of the plurality of extended positions comprising a radial configuration whereby the plurality of blades are forced to slide through an end cap coupled to a distal portion of the elongate sheath, the end cap comprising a plurality of openings disposed around a circumference of the end cap through which the plurality of blades are individually extended, each of the plurality of openings defining an angle for deflecting the plurality of blades during extension through the plurality openings;

the plurality of elongate blades being deflectable in at least one direction along their entire length for continuous adjustment of the plurality of blades between the retracted position and the plurality of extended positions.

2. A cavity drill as recited in claim 1, wherein at least a portion of the cavity drill is radiolucent.

3. A cavity drill as recited in claim 1, further comprising radio opaque markers configured for determination of size and length of a cavity being created during a fluoroscopy procedure.

4. A cavity drill as recited in claim 1, wherein the body is formed of the radiolucent material and the sheath and the cutting tool are formed of a radio opaque material.

5. A cavity drill as recited in claim 1, further comprising a handle extending from the body, the handle being connected with the cutting tool wherein the handle is manipulable in a configuration that causes deployment of the plurality of blades between the retracted position and one or more of the plurality of extended positions.

6. A cavity drill as recited in claim 5, wherein the handle is operatively connected to the cutting tool via gearing disposed within the body.

7. A cavity drill as recited in claim 1, wherein the sheath is configured to rotate in an oscillating configuration such that the distal end rotates in a clockwise direction and a counterclockwise direction.

8. The cavity drill as recited in claim 6, wherein;
the gearing disposed within the body is operatively coupled to an external motor for rotating the elongate sheath relative to the body.

9. A cavity drill configured for use with a bone drill as recited in claim 1, wherein the plurality of blades extend from a distal portion of the elongate sheath and are configured to rotate in an oscillating configuration such that the plurality of blades rotate in a clockwise direction and a counterclockwise direction.

10. A cavity drill configured for use with a bone drill as recited in claim 1, wherein the cutting tool is configured for axial movement relative to the elongate sheath.

11. A cavity drill configured for use with a bone drill as recited in claim 10, wherein the axial movement is spring driven to facilitate impact engagement of the cutting tool with bone of vertebral body.

12. A cavity drill configured for use with a bone drill as recited in claim 8, wherein the gearing is configured to convert a rotation of the external motor to oscillation of the plurality of blades.

13. A cavity drill configured for use with a bone drill as recited in claim 12, wherein the plurality of blades excises a defined arc in bone.

14. A cavity drill configured for use with a bone drill as recited in claim 13, wherein the defined arc is approximately 60 degrees.

15. A cavity drill configured for use with a bone drill as recited in claim 1, wherein the body includes a handle comprising snapping features for releasable coupling to a bone drill.

16. A cavity drill configured for use with a bone drill as recited in claim 10, wherein the plurality of blades are deployed from the retracted position within the elongate sheath to one or more of the extended positions by a pusher axially disposed within the elongate sheath.

17. A cavity drill configured for use with a bone drill as recited in claim 1, wherein the plurality of blades have radio opaque markers to increase conspicuity.

18. A cavity drill configured for use with a bone drill as recited in claim 9, wherein the plurality of blades are configured to resist deflection in the direction of rotation.

19. A cavity drill configured for use with a bone drill as recited in claim 1, wherein the plurality of blades are driven at variable speeds.

20. A cavity drill configured for use with a bone drill as recited in claim 1, wherein the end cap further comprises distal ball top coupled to a conical body, the plurality of openings disposed around the circumference of the distal ball top, the conical body being axially disposed within the elongate body and comprising a plurality of guides for directing the plurality of blades through the plurality of openings within the ball top.

21. A cavity drill configured for use with a bone drill as recited in claim 16, wherein the pusher comprises a tube whereby a distal portion of the tube is cut to create the plurality of elongate blades.

* * * * *